(12) United States Patent
Hohla et al.

(10) Patent No.: US 7,237,898 B1
(45) Date of Patent: Jul. 3, 2007

(54) CUSTOMIZED CORNEAL PROFILING

(75) Inventors: Kristian Hohla, Vaterstetten (DE); Gerhard Youssefi, Landshut (DE); Charles R. Broadus, Bothell, WA (US); Timothy N. Turner, West Jordan, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 411 days.

(21) Appl. No.: 10/110,922

(22) PCT Filed: Oct. 20, 2000

(86) PCT No.: PCT/EP00/10375

§ 371 (c)(1),
(2), (4) Date: Feb. 3, 2003

(87) PCT Pub. No.: WO01/28410

PCT Pub. Date: Apr. 26, 2001

(30) Foreign Application Priority Data

Oct. 21, 1999 (DE) .............................. 199 50 790
Mar. 23, 2000 (DE) .............................. 100 14 480

(51) Int. Cl.
*A61B 3/00* (2006.01)
*A61B 3/103* (2006.01)
*A61B 3/107* (2006.01)

(52) U.S. Cl. ........................... 351/246; 351/205; 606/5
(58) Field of Classification Search .............. 351/200, 351/205, 206, 211, 212, 246, 214, 221; 606/4–6, 606/10; 607/53–54
See application file for complete search history.

(56) References Cited

U.S. PATENT DOCUMENTS

| 4,692,003 | A | | 9/1987 | Adachi et al. |
| 5,418,714 | A | | 5/1995 | Sarver |
| 6,070,981 | A | | 6/2000 | Mihashi et al. |
| 6,106,188 | A | | 8/2000 | Menezes et al. |
| 6,234,631 | B1 | * | 5/2001 | Sarver et al. ............... 351/212 |
| 6,305,802 | B1 | * | 10/2001 | Roffman et al. ............ 351/212 |
| 6,402,319 | B1 | * | 6/2002 | Broadus .................... 351/212 |

(Continued)

FOREIGN PATENT DOCUMENTS

| AU | 64412/00 B | 8/2000 |
| EP | 0947158 A | 10/1999 |
| JP | 11137520 A | 5/1999 |
| WO | WO 9201417 A | 2/1992 |

OTHER PUBLICATIONS

Pallikaris et al., "Photorefractive Keratectomy with a Small Spot Laser and Tracker," Jour. pf Refr. Surgery, Mar./Apr. 1999, pp. 137-144.

(Continued)

*Primary Examiner*—Scott J. Sugarman
*Assistant Examiner*—DaWayne A. Pinkney

(57) ABSTRACT

A customized corneal profile is provided by combining corneal topography data with captured wavefront aberration data to form a course of refractive treatment of the eye. In one embodiment, the captured wavefront data is employed within the area of a pupil, while the corneal topography data is employed in the area outside of the pupil. In other embodiments, the topography data is adjusted based on the wavefront data, a course of refractive treatment is simulated and displayed upon the topography data, and an initial evaluation of the suitability of a patient for treatment is performed based on the topography data.

35 Claims, 15 Drawing Sheets

U.S. PATENT DOCUMENTS

| | | | | |
|---|---|---|---|---|
| 6,413,251 | B1* | 7/2002 | Williams | 606/5 |
| 6,428,168 | B2* | 8/2002 | Sarver et al. | 351/212 |
| 6,500,171 | B1* | 12/2002 | Williams et al. | 606/5 |
| 6,508,812 | B1* | 1/2003 | Williams et al. | 606/5 |
| 6,609,793 | B2* | 8/2003 | Norrby et al. | 351/212 |
| 6,634,752 | B2* | 10/2003 | Curatu | 351/212 |
| 2003/0069566 | A1* | 4/2003 | Williams et al. | 606/5 |
| 2003/0142271 | A1* | 7/2003 | Ross et al. | 351/212 |
| 2004/0075807 | A1* | 4/2004 | Ho et al. | 351/160 R |
| 2004/0246440 | A1* | 12/2004 | Andino et al. | 351/177 |

OTHER PUBLICATIONS

Cimberle, "Corneal Asphericity Vital in Preventing Postop Aberrations," Ocular Surgery News, OSNSupersite.com, (Aug. 1, 2001).

Schmitt, Jr., "Choosing the Right Corneal Topographe for Your Practice," Ocular Surgery News, Slackinc.com, (Nov. 15, 1997).

Belin et al., "The Par Technology Corneal Topography System," Refr. & Corneal Surgery, Jan./Feb. 1992, pp. 88-96.

Sun et al., "The Change in Wave-Front Aberrations of the Eye with Age for Chinese School Children and Young Adults," Opt. Abberrations in Myopia, p. 132.

Thorn, et al., "The Vision of Myopic Children: How Wavefront Aberrations Alter the Retinal Image of School Book Text," Opt. Aberrations in Myopia, p. 127.

He, et al., "Wave-front Aberrations in the Eyes of Myoptic and Emmetropic School Children and Young Adults," Opt. Aberrations in Myopia, p. 113.

Marcos, et al., "Do Myopic Eyes Suffer from Larger Amount of Aberretions ?," Opt. Aberrations in Myopia, p. 118.

Cheng, et al., "Increased Optical Aberrations in Myopia," Opt. Aberrations in Myopia, p. 122.

Thibos, et al., "The Chromatic Eye: A New Reduced-Eye Model of Ocular Chromatic Aberration in Humans," Applied Optics, vol. 31 (No. 19), p. 3594-3600, Jul. 1, 1992).

Noack, et al., "Influence of Ablation Plume Dynamics on the Formation of Central Islands in Excimer Laser Photofractive Keratectomy," Ophthalmology, May 1997, vol. 104 (No. 5), pp. 823-830.

Van De Velde et al., "Scanning Laser Retinoscopy: A New Technique for Evaluating Optical Properties of the Cornea After Refractive Surgery," SPIE, vol. 3192, pp. 187-194, (Sep. 4, 1997).

Herzig, et al., "Custom Ablation Studies Have Shown Excellent Results," Ocular Surgery News, Slackinc.com, (Sep. 1, 2000).

Alpins, et al., "Is the Future of Refractive Surgery Based on Corneal Topography or Wavefront?," Ocular Surgery News, Slackinc.com (Aug. 1, 2000).

Arons, et al., "Customized Ablations: Getting Closer Yet," Ocular Surgery News, Slackinc.com, (Aug. 1, 2000).

"Corneal Topography and Wavefront Analyzers in the New Century," Ocular Surgery News, Slakinc.com, (Aug. 1, 2000).

Seilor, "Wavefront-Guided LASIK can Decrease Aberrations and Increase Visual Acuity," Ocular Surgery News, Slackinc.com, (Sep. 1, 2000).

Moran, "Method of Estimating Corneal Thickness after LASIK should Improve Safety," Ocular Surgery News, Slackinc.com, (Oct. 15, 2000).

Arons "Customized Ablations: The Future is Close," Refractive Surgery, Slackinc.com, (Feb. 15, 2000).

Casebeer, et al., "Topography, Excimer Makers Seek Custom Ablation Methods," Ocular Surgery News, Slackinc.com, (Dec. 1, 1998).

Marshall, et al., "Photoablative Reprofiling of the Cornea Using an Excimer Laser: Photorefractive Keratectomy," Lasers in Ophthal., 1986, vol. 1 (No. 1), pp. 21-48.

Burstein, et al., "Corneal Healing After Excimer Laser Surface Ablation," SPIE, 1988, pp.57-64.

Yoder, et al., "Beam Delivery System for UV Laser Ablation of the Cornea," SPIE, 1988, p.77-82.

Shimmick, et al., "Corneal Ablation Profilometry and Steep Central Islands," Jour. of Refr. Surgery, May/Jun. 1997, pp. 235-245.

Keller et al., "Computer Simulation of Centration Effects on Corneal-Topography Analysis of Excimer Laser Photorefractive Keratectomy Ablations," Cornea, vol. 16 (No.1), pp. 54-63.

Roberts, "Corneal Topography: A Review of Terms and Concepts," Cataract Refract. Surg., Jun. 1996, pp. 624-629.

Seitz, et al., "Correction of Irregular Corneal Astigmatism Using Topography-Based Flying-Spot Laser Photoablations," www.onjoph.com/new/correction-body.html.

Dausch, et al., "Topographic-gefuhrte Excimer-Laser-Ablation," der Augenspiegel, Jun. 1999, pp. 8-16.

Buratto, et al., "LASIK Surgical Techniques and Complications," LASIK Correction of Irregular Astigmatism, pp. 487-489.

Klein, "Optimal Corneal Ablation for Eyes with Arbitrary Hartmann-Shack Aberrations," Optical Society of America, Sep. 1998, vol. 15 (No. 9), pp. 2580-2588.

* cited by examiner

CUSTOMIZED CORNEAL PROFILING

TECHNICAL FIELD

The invention relates to systems for ophthalmic refractive surgery, and more particularly to a system for combining ophthalmic wavefront aberration data and ophthalmic corneal topography data to create a customized ablation correcting profile.

BACKGROUND ART

The field of ophthalmology for the past number of years has seen great strides in the development of refractive treatments intended to correct the vision of the eye. These techniques have evolved from the earlier radial keratotomy technique, in which slits in the cornea allowed the cornea to relax and reshape, to present techniques including photorefractive keratectomy ("PRK"), anterior lamellar keratectomy ("ALK"), laser in situ keratomileusis ("LASIK"), and thermal techniques such as laser thermal keratoplasty ("LTK"). All of these techniques strive to provide a relatively quick but lasting correction of vision.

With the development and refinements of these techniques, greater precision has become possible in refractive error correction. In early types of treatments, the precision of the correction was relatively coarse. To provide correction to within plus or minus one diopter of the desired correction for myopia, for example, would be considered an excellent outcome. The types of treatments have become progressively refined, however, allowing more subtle defects to be corrected. Myopia and hyperopia can now be corrected to a high degree of precision with current techniques, and using excimer lasers, higher order defects can also be corrected, such as asphericity and irregular astigmatism.

At the same time, the diagnostic tools to determine what correction is needed have also advanced. Employing topography systems, vision defects can be determined and corrected irrespective of their "regularity". Such techniques are described in U.S. Pat. No. 5,891,132, entitled "Distributed Excimer Laser Surgery System," issued Apr. 6, 1999. A variety of new topography systems, pachymetry systems, wavefront sensors, and overall refractive error detection systems can detect not only the amounts of myopia, hyperopia, and astigmatism, but also, higher order aberrations of the refractive properties of the eye.

Detection of wavefront aberrations in the human eye for such purposes as intraocular surgery and contact lens and intraocular lens fabrication is disclosed, e.g., in Liang et al, "Objective measurement of wave aberrations of the human eye with the use of a Hartmann-Shack wave-front sensor," *Journal of the Optical Society of America*, Vol. 11, No. 7, July, 1994, pp. 1–9. That technique will be summarized with reference to FIG. 1. A beam of light from a laser diode or other suitable light source is directed toward the pupil and is incident on the retina A beam (or wavefront, as described in FIG. 1) is reflected by the retina and emerges from the pupil. Typically, the incoming and emergent light follow a common optical path; the incoming light is brought into the common optical path with a beamsplitter. The emergent beam is applied to a Hartmann-Shack detector to detect the aberrations. Such a detector includes an array of lenslets which break up the light into an array of spots and focus the spots onto a charge-coupled detector (not shown in FIG. 1) or other two-dimensional light detector. Each spot is located to determine its displacement $\Delta$ from the position which it would occupy in the absence of wavefront aberrations, and the displacements of the spots allow reconstruction of the wavefront and thus detection of the aberrations through known mathematical techniques. In FIG. 1, $\theta$ is the locally averaged wavefront slope in front of the lenslet array and is related to the spot displacement and the lenslet focal length by $\theta = \Delta/f$, as will also be appreciated by those skilled in the art.

Improvements to the technique of Liang et al are taught in J. Liang and D. R. Williams, "Aberrations and retinal image quality of the normal human eye," *Journal of the Optical Society of America*, Vol. 4, No. 11, November, 1997, pp. 2873–2883 and in U.S. Pat. No. 5,777,719 to Williams et al. ("Williams"). Williams teaches techniques for detecting aberrations and for using the aberrations thus detected for eye surgery and the fabrication of intraocular and contact lenses.

International Patent Publication WO 99/27334 (International App. PCT/UUS97/21688)("Frey") teaches a further variation using polarizing optics to control back-scatter from the lenses in the detector setup. Like Williams, Frey suggests using data from the wavefront sensor to develop an optical correction for the eye examined. More specifically, the optical correction so determined is limited to the aperture of the cornea measured by the sensor, e.g., the 6 millimeter circle to which the eye's pupil was dilated when the eye was measured. Outside that area, Frey suggests using a tapering blend zone of partial ablation to minimize severe changes in corneal curvature and hence lessen regression.

These diagnostic systems and techniques have the potential for permitting correction of both the fundamental and higher order defects, especially when used with the even more refined refractive correction techniques, with the possibility that vision correction to better than 20/20 will someday be the norm. However, improved techniques for applying advancing diagnostic technology to refractive surgery are needed.

SUMMARY OF THE INVENTION

In the system and according to the techniques of embodiments of the invention, a wavefront aberration diagnostic tool for ophthalmic evaluation is coupled to an ophthalmic topography tool. Refractive data within the bounds of the pupil is gathered by the wavefront tool and with data extending beyond the bounds of the pupil gathered by the topography tool. This information is then combined, either before or after it is employed to create a refractive treatment. Preferably this treatment is created for an excimer laser surgery system.

Additional embodiments of the invention provide further techniques to combine wavefront and topography data and to employ both in the course of treating refractive errors of the eye. In one embodiment, the topography data permits a pre-evaluation or pre-screening of patients based on a variety of criteria, such as corneal thickness, corneal asymmetry, and similar parameters. If the patient is a suitable candidate, the wavefront tool is used to capture the eye's wavefront aberration. Then the captured wavefront aberration data is used to calculate an ablation profile. That ablation profile is then simulated on the captured topographic data of the eye, and the resulting simulated ablation is also evaluated to determine whether the outcome (again, such as corneal thickness and irregularity) will fall within acceptable guidelines. Thus, the topographic data representing physical refractive characteristics of the eye and wavefront data representing overall optical refractive characteristics of the eye are used in evaluating and generating the ablation profile.

In another embodiment, the topography of the various features of the eye, such as the front and back of cornea and the front of the lens, is captured by an elevation based topography system. A calculated wavefront ablation is then derived based on that topography data using a ray tracing system. A wavefront tool then captures the overall wavefront aberration of the optical components of the eye within the pupil area. Then, by comparing the calculated wavefront based on the eye's topography with the captured wavefront from the wavefront tool within the pupil area, the topographically derived calculated wavefront is "tuned" based on the captured wavefront data within the pupil area. This allows an overall wavefront, and corresponding treatment, to be developed for areas within and without the pupil area, while "tuned" by the captured wavefront data within the pupil area. Because the captured wavefront data captures overall refractive error of the optical components of the eye, while the topography data used to calculate the wavefront may lack the topography of certain surfaces, the captured wavefront data thus provides a good basis to which to calibrate the calculated wavefront.

In yet another embodiment, for extremely irregular eyes, first a course of treatment is generated using the topographic data to attempt to remove gross asymmetries or irregularities in the refractive profile. Once that treatment has been applied, a refractive evaluation is then performed with either the topographic tool or the wavefront tool, or both, to provide a basis for further refractive correction of the eye.

Similarly, in highly irregular eyes, it may be difficult to capture or determine the source of centroids captured by a wavefront tool. The centroids may be so irregularly displaced as to be difficult to determine which centroid is associated with which portion of the eye. In such an eye, the topographic data and the ray tracing algorithm permit the centroid location to be estimated. Then, the wavefront sensor captures centroids, and based on the calculated centroids from the topographic data, the actual centroid locations are associated with particular areas of the eye. In this way, wavefront data for even highly irregular eyes can be better captured.

All of these various embodiments thus permit the use of both wavefront and topographic data to develop refractive treatments. Further, various aspects of these embodiments can be combined or eliminated, but generally, these embodiments are alternative combinations permitting development of refractive treatments based on both topographic data and wavefront data.

According to further features of the invention, the topography system is preferably an elevation based, slit lamp topography tool that determines the elevation of refractive surfaces within the eye, including both the front and back corneal surfaces. From this data, the topography system preferably employs ray tracing to derive an overall refractive characteristic of the eye, both within and without the pupil area.

MODE(S) FOR CARRYING OUT THE INVENTION

Figure 1:
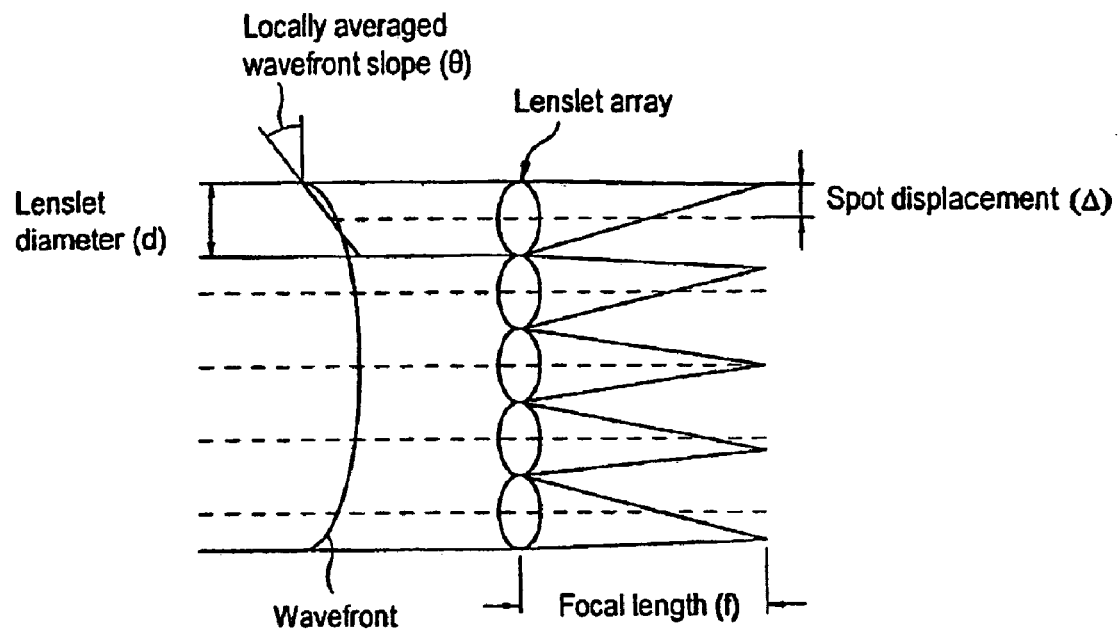
FIG. 1 illustrates principles involved in wavefront measurement.
Figure 2:
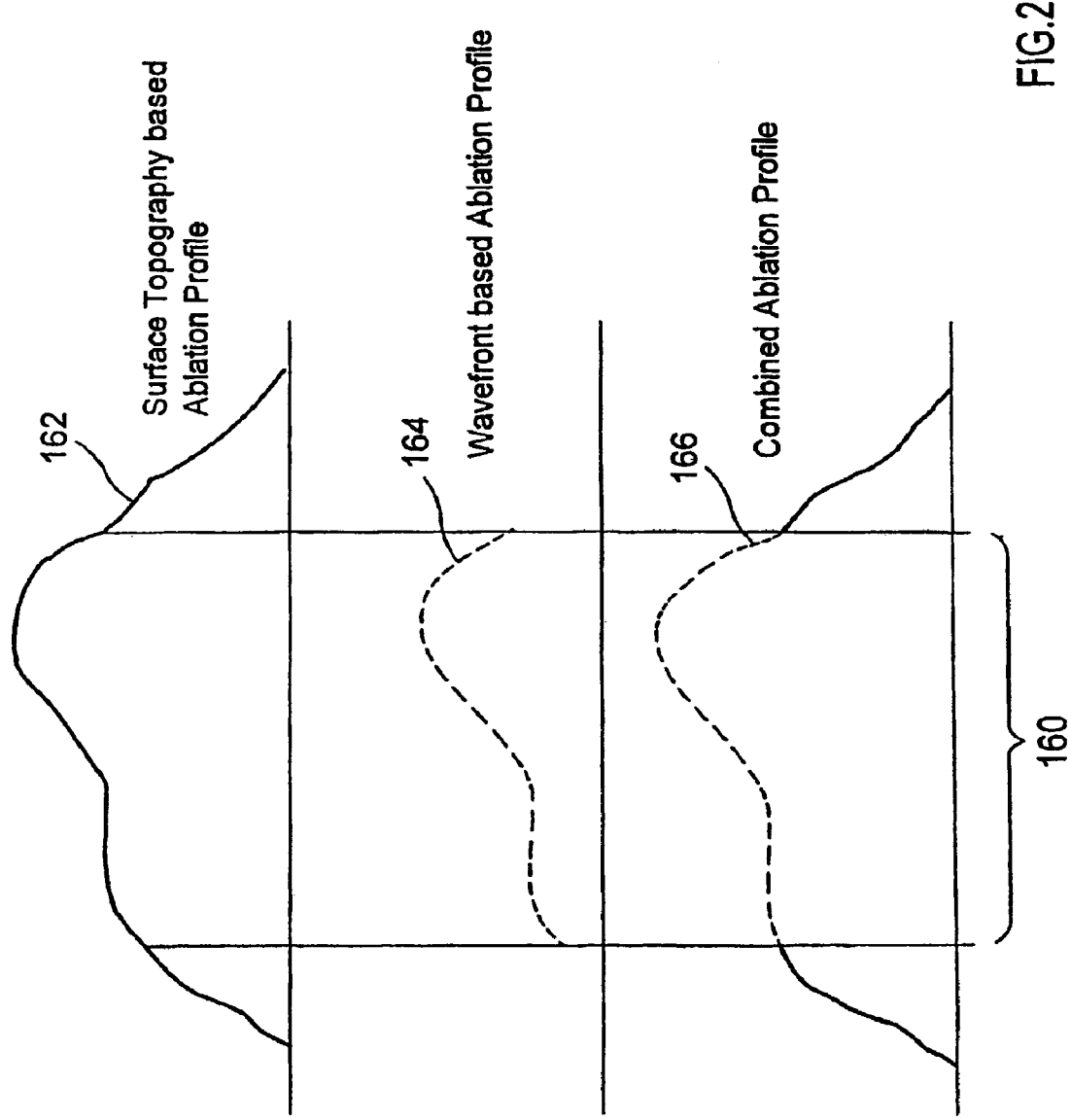
FIG. 2 is a diagram illustrating combined ablation profiles developed from wavefront data and from surface topography data.

Corneal surface topography systems produce surface topography data regardless of the amount of dilation of the pupil, but the area over which wavefront sensors collect data is limited by the dilation of the pupil when the measurement is taken. Wavefront sensors measure refractive effects of optical elements that are in the optical path. In accordance with certain aspects of the invention, a corneal surface topography system measures a surface area larger than the dilated pupil, while a wavefront sensor measures a central portion within the area of the pupil. The technique is illustrated in FIG. 2, in which ablation profiles based on wavefront data and surface topography data are combined. FIG. 2 shows a surface topography based ablation profile 162 developed from surface topography data. This data is valid even outside of the pupil, illustrated as a pupil diameter 160. To compare, a wavefront based ablation profile 164 developed from wavefront data is generally only valid within the area of the pupil diameter 160. So, the two are illustrated as a combined ablation profile 166 by using the wavefront based ablation profile 164 within the pupil diameter 160 and using the surface topography based ablation profile 162 outside of the pupil diameter 160. In this example, each ablation profile is first calculated from the corresponding data before the profiles are combined. Other techniques could alternatively combine the captured data before an ablation profile itself was calculated. Elevation-based topography systems such as the ORBSCAN II® topography system available from Bausch & Lomb/Orbtek, Inc. of Salt Lake City, Utah, are especially advantageous when used with the wavefront sensor. However, other topography systems, such as curvature based systems, could be useful in the practice of this invention, although preferably through measurement of more than only the eye's front surface. Other types of systems that are useful include dual camera systems such as described in U.S. Pat. Nos. 5,159,361 and 4,995,716.

The ORBSCAN II® topography system is a slit-scan elevation based, topography system that simultaneously measures both surfaces of the cornea as well as the front of the lens and iris. Each measured surface can be displayed as maps of elevation, inclination, curvature or power. A full-corneal map of pachymetry is also derived from the measured surfaces of the cornea. Raytraced optical computations can be used to ascertain the visual effect of the various optical components within the ocular anterior segment. ORBSCAN II® topography measurements are based on diffuse reflections rather than specular reflections, to precisely detect the surface height rather than surface curvature. Use of a specularly reflected image from a placido or other reflective target to measure surface slope can be used in combination with measurement of diffuse reflections as will be apparent to those skilled in the art. For illustrative descriptions of the elevation-based, ORBSCAN II® topography system, see U.S. Pat. Nos. 5,512,965 and 5,512,966 by Richard K. Snook. Data from the ORBSCAN II® system can be accurately and seamlessly transitioned into the overall refractive data from the wavefront sensor.

It is also possible for data from the wavefront sensor to be used to "calibrate" data in the topography system. Because the wavefront sensor describes the overall refractive error in the eye, it can allow the software for the topography system to correlate a surface topography at any particular point with an overall refractive error (determined by a wavefront sensor) associated with those points. Thus calibrated, the topography system data can then be used to create an overall refractive error profile.

As another example, the data from various diagnostic tools can be combined to provide an overall model of the optical elements in the eye. For instance, a corneal surface topography system could provide surface data, an ultrasonic system could provide corneal thickness data, and a wavefront sensor could provide overall refractive error data. By "subtracting out" the effects of the surface data and the thickness data, optical elements past the cornea thus can be modeled using the various sets of data. Moreover, ultrasonic imaging and optical coherence tomography (OCT) allows one to measure not only the surface topography (anterior surface), but also the epithelial-stromal interface. Since the stromal layer is the actual treatment layer, the stromal interface is the important surface for predicting the stromal tissue laying below.

Figure 3:
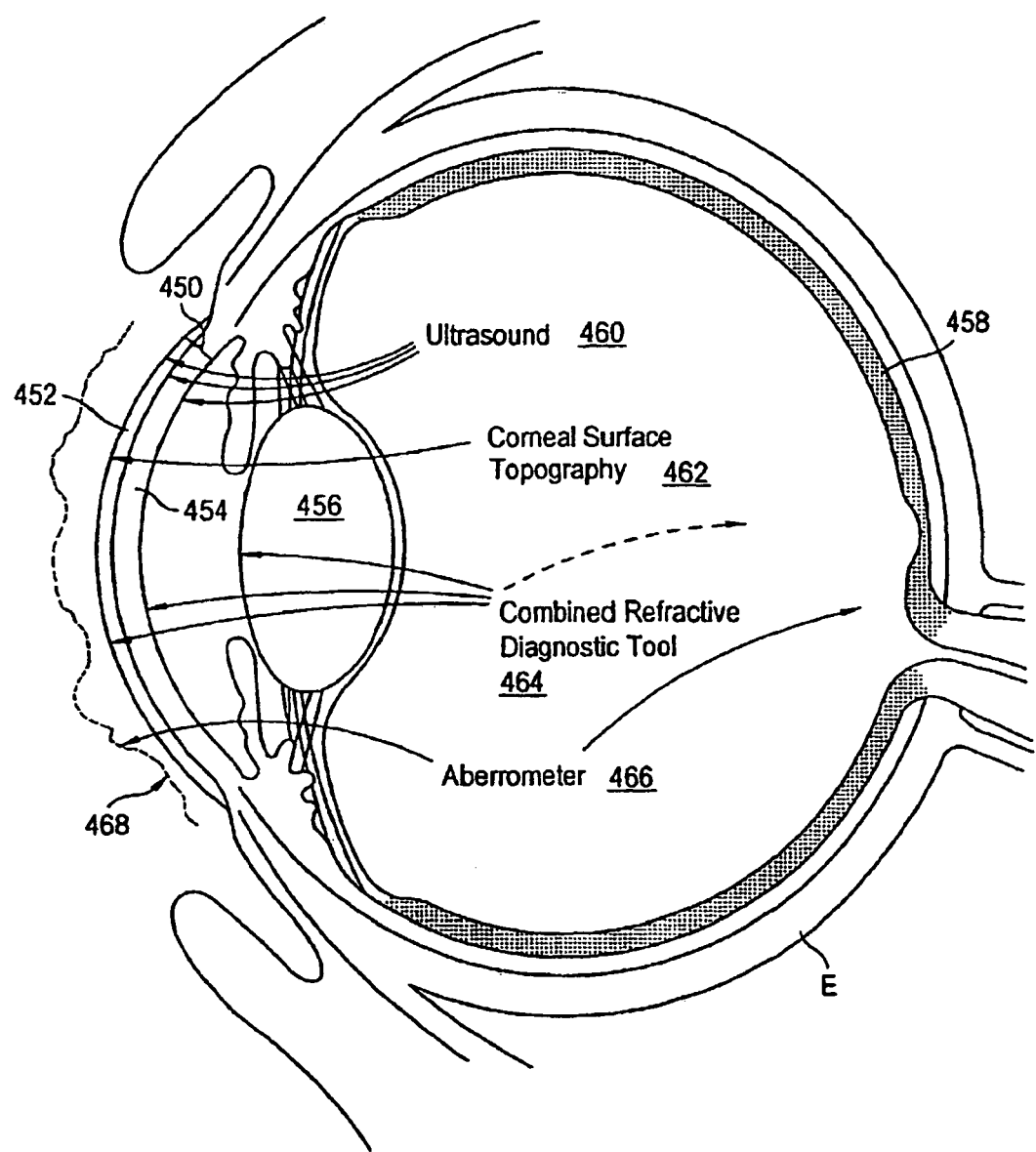
FIG. 3 is a cutaway representation of an eye, as well as associated diagnostic tools used to determine particular refractive characteristics of the eye.

Turning to FIG. 3, a cross-sectional view is shown of the eye E including a cornea 450, a lens 456, and a retina 458. The cornea 450 includes a number of layers, such as epithelium 452 and stroma 454. These various components, particularly the cornea 450 and the lens 456, combine to form an overall refractive (optical) power and a refractive characteristic for the eye E. A number of factors can contribute to refractive (e.g., wavefront aberration) errors, including, but not limited to, irregularities in the cornea 450 or in the lens 456, and the distance (e.g., in the sense of a defocusing aberration) from the cornea 450 and lens 456 to the retina 458.

Also illustrated in FIG. 3 are notations indicating various types of diagnostic tools particularly suited to analyze refractive and other characteristics of particular portions of the eye E. These tools can provide different types of data for different portions or components of the eye E. For example, ultrasonic techniques 460 can typically determine the thicknesses of the epithelium 452 and the stroma 454, which provide the overall thickness of the cornea 450. There are a variety of ultrasonic techniques that can be used, including a pachymeter as well as a technique described in U.S. Pat. No. 5,293,871, entitled "System for Ultrasonically Determining Corneal Layer Thickness and Shape," issued Mar. 15, 1994.

Corneal surface topography systems 462 typically provide and analyze corneal surface topography. Topography systems, such as the previously made ORBSHOT™ by Orbtek and System 2000 by EyeSys, typically exhibit a very high resolution, but are restricted to the surface of the epithelium 452 of the cornea 450.

A combined refractive diagnostic tool 464, such as the ORBSCAN II® topography system by Orbtek, typically determines and analyzes a variety of thicknesses and surfaces within the eye. This can include the thickness of the cornea 450, the surface topography of the cornea 450, the surface of the lens 456, the distance from the lens 456 to the cornea 450, and the distance from these front optics of the eye to the retina 458.

Finally, in FIG. 3, a wavefront sensor, illustrated by 466, such as the previously described wavefront sensor 102 or the wavefront sensor in Williams, provides data on the overall refractive aberrations of the eye, shown as an aberrated wavefront profile (data) 468. The wavefront sensor techniques are empirical in nature—concerned with characterizing the wavefront of light external to the eye that was reflected from the retina 458 rather than with the physical characteristics of any particular optical component of the eye E.

Figure 4A:
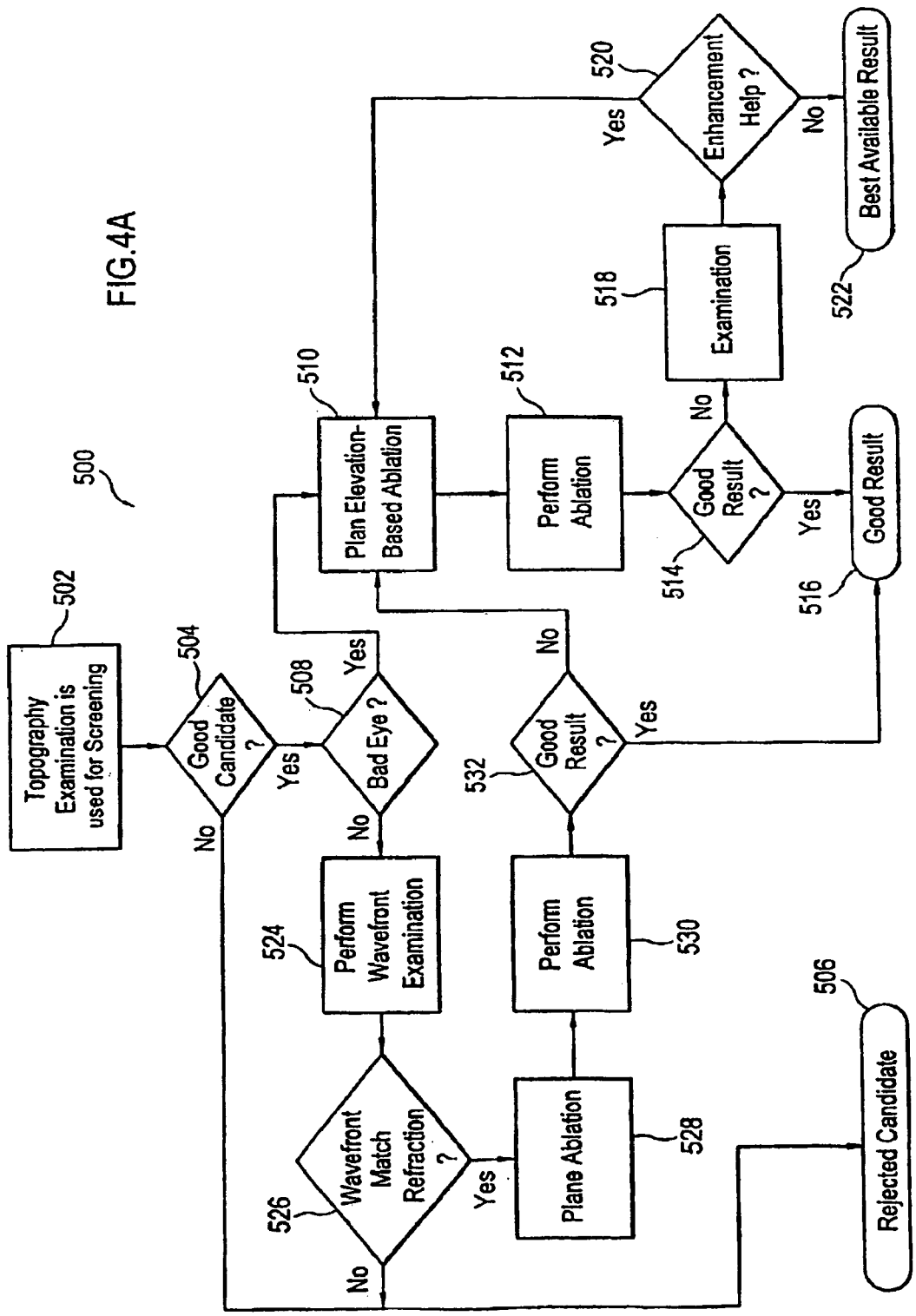
FIGS. 4A and 4B are flow diagrams illustrating both patient evaluation flow and process/data flow of a combined topography/wavefront treatment system according to embodiments of the invention.
Figure 4B:
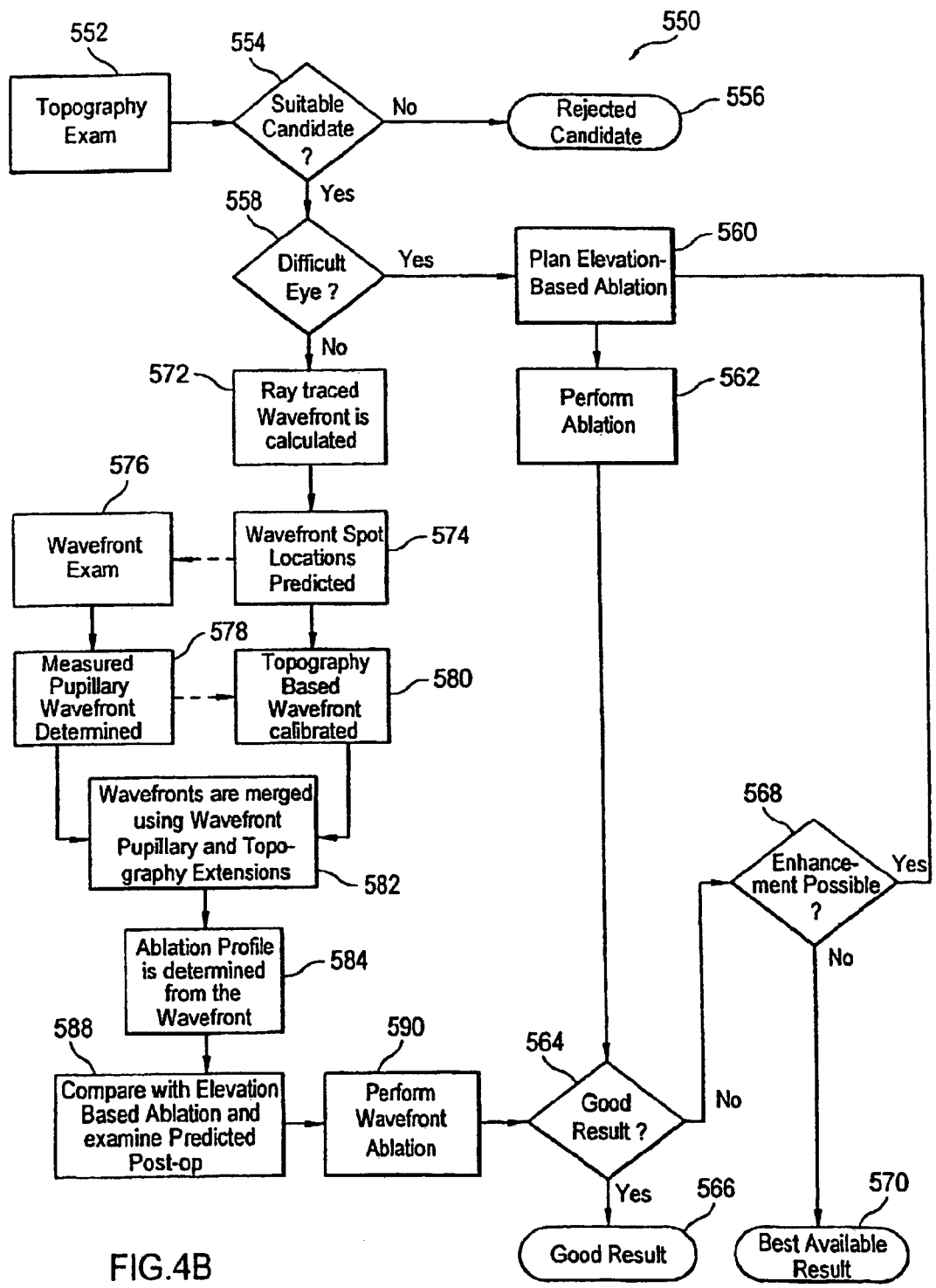

Turning to FIGS. 4A and 4B, illustrated respectively, are a patient flow diagram 500 and a process/data flow diagram 550 illustrating embodiments according to the invention in which both topography data and wavefront data are combined in developing a treatment for refractive correction of the eye. Preferably, the topography system is an ORBSCAN II® topography system by Orbtek, which as discussed above provides the elevation-based topography of various surfaces. Further, the topography system can employ a ray tracing module to calculate a wavefront based upon the physical components of the eye as determined by the topography system. The ORBSCAN II® topography system, however, does not determine the physical structure of all of the components of the eye, so an "overall refraction" is determined, such as from the patient's manifest refraction, as a "baseline" from which the topography Rayscan module determines the overall wavefront aberration of the patient's eye.

In conjunction with this topography tool, a wavefront tool such as the previously described wavefront sensor 102 or the wavefront sensor in Williams or others, provides data for the refractive wavefront aberration. This data has the advantage of determining the overall refractive characteristics of the eye, whereas the topography based system may lack the physical parameters of certain components helpful to calculating the wavefront aberration of a patient's eyes, such as the shape of the back surface of the lens, and the exact optical refractive characteristics of corneal material.

Turning to FIG. 4A, in a typical evaluation and treatment, first a topographic examination is taken of the patient's eye and used for screening in a step 502. Because the topography system can determine certain parameters such as corneal thickness, bulging, and other physical parameters that could lead to an outright rejection, physically unsuited eyes are rejected at a step 504, such that baseline physically unsuitable eyes are rejected as indicated by the rejected candidate at step 506.

If, however, the topographic evaluation determines the physical characteristics of the patient eye may be suitable for developing a course of refractive treatment, the topographic data is then used to determine whether the eye is unsuitable for use of a wavefront tool—that is whether the eye is a "difficult," or "bad," eye. In such a case, the topography data rather than captured wavefront data may be used to generate a desired course of treatment. The patient proceeds to a step 510, where the appropriate ablation profiles are determined based on the topography data for the eye. Note as discussed below in conjunction with FIG. 4B, if the initial treatment based on the topographic data results in a much improved "good" eye, a subsequent course of treatment can be performed based on combined topography and wavefront data. But generally, starting with a "bad" eye, the course of treatment is developed using the elevation-based topography and then the ablation is performed at a step 512. If (step 514) the result is determined to be good, a favorable patient result occurs at step 516. If at step 514 the result is determined not to be optimal, another topographic examination is performed at step 518 to determine whether additional treatment would be helpful (step 520). If not, the patient's outcome, although not optimal, is final at step 522. But if so, another elevation based ablation is planned at step 510. Note that in this last course, if the topographic evaluation at step 518 indicates that the eye is no longer a "bad" eye, it is possible to return to step 508, where a wavefront based course of treatment is developed.

While the foregoing embodiment discusses a topography only based ablation for "bad" eyes, other approaches may use wavefront results even for "bad" eyes. The point is that different courses of treatment may be indicated for irregular eyes as opposed to more standard eyes. For example, it may be desired to perform a multi-staged correction for such "bad" eyes, as is discussed in assignee's concurrently pending "Method and Apparatus for Multi-Step Correction of Ophthalmic Refractive Errors."

Note that a period of time can pass between these evaluations. The stromal tissue that is cut when flaps are created in a LASIK procedure generally does not heal, so a flap can easily be relifted. So after normal edema on the patient's eye recedes after some period of days, the patient can then be evaluated to determine first whether their eye is still good or bad and second, whether additional treatment would be beneficial.

Suppose that at step 508 the patient does not have a "bad eye," either after the initial evaluation at step 504 or perhaps after the evaluation at step 518. In that case, a combined wavefront topography course of treatment is developed. Proceeding to step 524, a wavefront and examination is performed on the patient's eye. This is preferably done using manifest refraction (that is, without dilating the eye) although cycloplegic refraction (that is, with dilation of the patient's eye and corresponding paralyzing of the accommodation reflex) can be used. In this event, it is preferable to wait approximately 15 minutes post-dilation for dilation induced aberrations to subside. At step 526, the captured wavefront refraction is compared to the patient's actual subjective refraction. If there is a significant difference, the treatment can be terminated if the doctor desires, resulting in a rejected candidate at step 506. Certain differences, as discussed in conjunction with FIG. 4B, can be used to calibrate and match the two sets of data. For example, second order aberrations (sphere and cylinder) can be scaled to the desired value to match the refractive data or for other purposes.

If the captured wavefront data has a reasonable match with the patient's subjective refraction, the procedure instead proceeds to step 528, where the ablation is planned. As discussed below in conjunction with FIG. 4B, this can be generated in a variety of ways, such as from the captured wavefront data alone or from a combination of the captured wavefront and topography data. The procedure then proceeds to step 530, where the ablation is performed. Then, at step 532, a positive result yields an acceptable patient outcome at step 516. If not, the patient can be further evaluated for elevation based ablation profiles at step 510, discussed above.

In the overall course of treatment, however, it will be appreciated that the physical eye characteristics obtained by the topography data allow an initial evaluation of the patient for treatment. Then, either topography data alone, or topography data and captured wavefront data are together used to develop the overall course of treatment for the eye.

It will further be appreciated that a variety of different types of topography systems or other systems for developing physical characteristics of the eye (such as pachymeters and the like) can be used in place of the topography system. Further, the captured wavefront tool can include a variety of captured wavefront type systems, including a Hartmann-Shack system described by Williams, scanning systems, a variety of other types of captured wavefront systems.

Turning to FIG. 4B, shown is the typical process/data flow chart 550 associated with the patient flow chart 500 of FIG. 4A. The process/data flow chart 550 of FIG. 4B is more particularly directed to typical data flow for topography data and captured wavefront data in developing a course of refractive treatment. As described above in conjunction with FIG. 4A, the data flow begins with a topography examination at a step 552, with the topographic data (preferably elevation data for multiple surfaces) resulting from that examination being reviewed at step 554 for suitability. The data can be examined both manually or automatically, and in combination with other data to determine the suitability of the patient's eye for a refractive treatment. A cornea that is too thin, an eye that is too irregular, or other criteria can lead to rejecting the patient, shown as a step 556. If the eye is suitable for treatment, however, the topography data is forwarded at a step 558 for an evaluation of whether this is a simple or difficult eye. This determination, too, can be based on a variety of criteria, and can be automatic, manual, or some combination with, for example, the doctor evaluating the displayed topography data. If the eye is a "difficult," or "bad," eye at step 558, the data flow proceeds to a step 560, where the topography data in conjunction, for example, with standard visual acuity data based on qualitative examination is employed to develop a standard course of refractive treatment based on the elevation data. Typically, such an elevation-based ablation profile only relies on both the patient refraction and the elevation map of the eye's surface to determine both a desired post-operative spherical corneal power and an ablation profile to yield that power. Such an elevation-based system could, however, take into account lenticular astigmatism, for example, if the lens profile is captured by the elevation based system. This topographic-based approach may be suitable where a wavefront sensor cannot provide reliable data due to problems with the patient's eye. Such problems can include irregularities and a variety of other conditions that affect the ability to actually capture the overall refractive captured wavefront.

As part of developing this course of refractive treatment, an appropriate laser shot pattern or other refractive treatment technique is developed, the treatment is simulated, and the resulting change in corneal profile displayed to the doctor. Because the initial eye surface profile is known from topography data, and because the effect of the course of refractive treatment is known, the resulting profile, thickness, and other physical topography characteristics of the eye are somewhat predictable and can be displayed to the doctor. If the doctor decides not to proceed with a course of treatment based on this display, the entire procedure can be terminated.

If the doctor decides to proceed with treatment, at step 562 the doctor performs the ablation. The course of treatment developed in the step 560 can be transmitted to the laser system in step 562 in a variety of ways, or the calculation could be performed as part of the laser system. U.S. Pat. No. 5,891,132 to Hohla describes a distributed system in which the courses of treatment are transmitted from location to location to better utilize resources; a similar system can be implemented for routing of the various refractive and ablation profile data in the disclosed system. In any case, the ablations are performed at step 562, whether PRK, LASIK, or another course of refractive treatment. Proceeding to step 564, the results are evaluated. This evaluation can be based on topography evaluation, a captured wavefront evaluation, or other refractive evaluations. If the resulting visual acuity is within desired limits, the patient's course of treatment is at an end as illustrated in step 566. Follow up evaluations can monitor for regression or other changes, both for the better or worse.

If at step 564 the results are determined not to be optimal, the patient can be evaluated for further enhancements at step 568. Again, this can be determined based on the same data gathered at step 564, or perhaps based on additional data. For example, at step 564 both the patient's manifest refraction can be determined using eye charts and topographic data can be gathered. At step 568, that data is analyzed, and if desired, additional captured wavefront data can be gathered. The data is then evaluated to determine if additional enhancements to the eye are possible. At this point, if enhancements are not possible, the patient's vision has been corrected as much as possible, so the course of treatment ends at step 570. If enhancements are possible, however, again an elevation based ablation is planned at step 560. Alternatively, and not shown, if the results as evaluated in steps 564 and 568 indicate that the eye is no longer a "difficult" eye, then a combined wavefront/topography course of treatment could instead be developed beginning at step 572.

The data gathered at each step can be forwarded for evaluation. That is, for example, in the result evaluation of step 564, any data gathered could be used at step 568 to determine possible enhancements. It may be desirable to wait a period of time until the eye has further stabilized before gathering the final data for a next course of treatment, but generally any captured data can be retained for a future step. It is also desirable to retain this captured data for clinical studies and evaluation of empirical results. Gathered into a database, this data forms an excellent repository of clinical information about the actual effects of certain courses of treatments on the eye, allowing nomograms to be adjusted to provide even better refractive correction for future patients.

Step 572 is begun when the eye is not a difficult eye at step 558, or possibly from step 568 if a previous treatment has resulted in a "easy" eye. In this embodiment, first a ray trace is performed on ORBSCAN II® topographic data to develop a calculated wavefront. This calculated wavefront is based on the physical topographies of optical components of the eye rather than being an actual captured wavefront by a wavefront tool. This calculated wavefront further allows the calculation of predicted wavefront centroids when the actual wavefront data is captured. This allows the captured wavefront data to be better evaluated and more varied wavefronts to be useable by the wavefront tool itself. At step 574, the centroids are in fact calculated and this data is preferably fed into the wavefront tool at step 576 to assist the wavefront tool in determining the source of actual spots. In many cases, the captured wavefront centroids will be regular enough such that the calculated wavefront data is not necessary, but the interaction of the two systems at step 574 and 576 does permit greater flexibility in the use of wavefront tools to determine refractive correction.

The wavefront examination at step 576 captures wavefront data at step 578 within the pupil area of the patient's eye. Many doctors prefer to base refractive correction on manifest refraction as opposed to cycloplegic refraction, and thus the pupil area may be relatively small when the wavefront data is captured, but this small area of data can provide highly precise complete refractive error within the pupil area. This data is then provided back to the topography data at step 580, where the topography-based calculated wavefront is "calibrated" or "tuned" based on the actual captured wavefront. Because an ORBSCAN II® based wavefront is an analytically calculated wavefront in which the topography system does not know all the physical parameters of the eye, the captured wavefront data can be used within the pupil area to tune and adjust the topography data within that pupil area. Based on the adjustment necessary within the pupil area, the topography-based calculated wavefront data is then correspondingly tuned outside the pupil area. This permits a "captured wavefront" based adjustment to the ORBSCAN II®-based calculated wavefront. Alternatively, using a darkened room, for example, a wavefront can be determined from a larger pupil area without inducing cycloplegia. In this case, the data could be used without the topography data, or it could be used in combination with the topography data.

Further, the actual captured wavefront data can be compared to the calculated wavefront data to ensure there are no gross discrepancies in the wavefronts. Such discrepancies could indicate, for example, a large irregularity in the optics of the eye not recognized by the topographic or wavefront data, and could suggest against continuing the procedure. For example, the topographic data assumes a fairly regular lens. Correction of an eye with a highly irregular lens could create problems if that lens were later replaced as part of a cataract surgery, for example. Assuming the wavefront within the pupil area as captured by the wavefront system and the wavefront in the pupil area as calculated by the topography system are relatively close, (and close to the subjectively determined refraction), albeit perhaps at a different scale, then the course of treatment proceeds. Together all of these sources of data thus act as a cross verification of each other.

Proceeding to step 582, the wavefront as measured by the wavefront tool is merged with the ORBSCAN II® based calculated wavefront. This can be done in a variety of ways. Either the ORBSCAN II® wavefront can be tuned, or scaled, based on the actual measured wavefront data as discussed above, or the measured wavefront can be used within the pupil area and the calculated wavefront used outside of the pupil area. However this data is combined, the overall wavefront is then provided to the ablation software at step 584 which calculates an appropriate course of treatment to correct for the wavefront error. This can be fully automated, or perhaps partially automated and partially manual.

Based on this calculation, a course of treatment is provided at step 586 for performing the ablation. This course of treatment is compared to a pure elevation based course of treatment (such as calculated in step 560) to ensure that the results are not highly disparate, which could indicate problems with performing a treatment on the eye. This step, too, acts as a cross check. Further, a simulation of the course of treatment is preferably performed on the topography as determined by the topography system to determine and display a resultant topography, and to verify that the resultant parameters of the treated eye are within acceptable norms.

Proceeding to step 590, the ablation is then performed. After the ablation is performed, a similar post-operative follow up evaluation is performed at step 564, and subsequent courses of treatment based on either topography, or captured wavefront, can be performed.

The computational system employed by the topography system, the wavefront tool, and the ablation profile generation tool can be separate, can be networked, can be combined, or some combination thereof. For example, in a typical implementation, both the ORBSCAN II® elevation based topography tool and the wavefront tool would employ a shared computational unit that gathers data from both and displays that data on a single screen. Alternatively, however, each tool could have its own computational system and display, with data being passed back and forth. Further, the course of treatment could be generated on the same system, on a stand alone personal computer, or within the laser system itself. Other alternatives for distribution of the computation and display of these various systems are possible.

Various wavefront techniques and associated devices sensors may be used in the practice of this invention and the following description is intended to be illustrative and not limiting. As described above, the Hartmann-Shack type sensor employs a lenslet array to develop an image of a number of spots on a detector. The displacements of the spots are related to localized slopes of the wavefront. How these fit to the first derivative of the Zernike polynomials provides the wavefront aberration data. The lenslet array provides a "parallel" retinal spot image point measurement. Another technique is a scanning technique in which a collimated beam or laser is focused on the retina and scanned across the eye. The reflected retinal image spot is then re-imaged onto a detector. For a perfect eye, all reflected image spots would fall on the detector center regardless of the location of the scan being on the cornea. The "displacement" of the image spots on the detector is measured as a function of scan position on the cornea, and the slope of the wavefront is determined similar to the Hartmann-Shack lenslet technique. Another technique provides for input beams that cross in the eye and focus on the retina. The reflected spots are imaged onto a detector and the "displacement" is determined relative to an emmetropic eye. All of these techniques, however, are similar in that they provide an actual wavefront measurement of the overall refractive error of the eye from the retina to the surface. Other wavefront techniques are known or could be developed.

Figure 12:
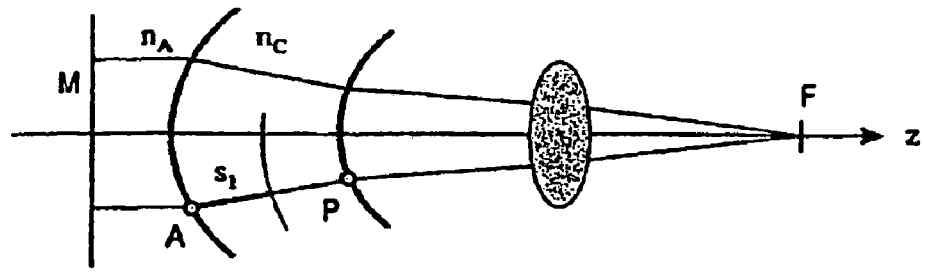
FIG. 12 is an illustration of optical raytracing for determining an ocular aberration.
Figure 13:
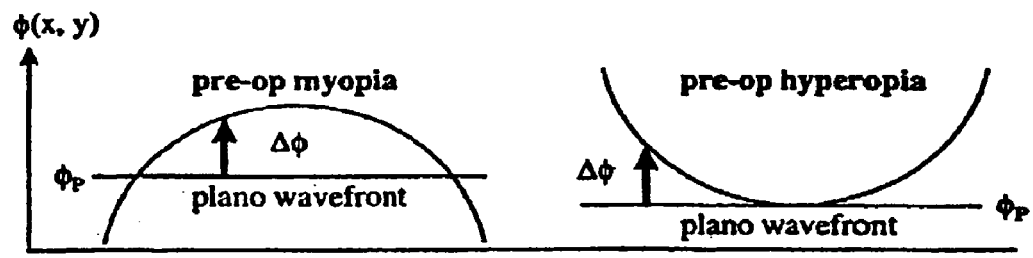
FIG. 13 is a schematic illustration of optical path length determination for a myopic and a hyperopic eye.
Figure 14:
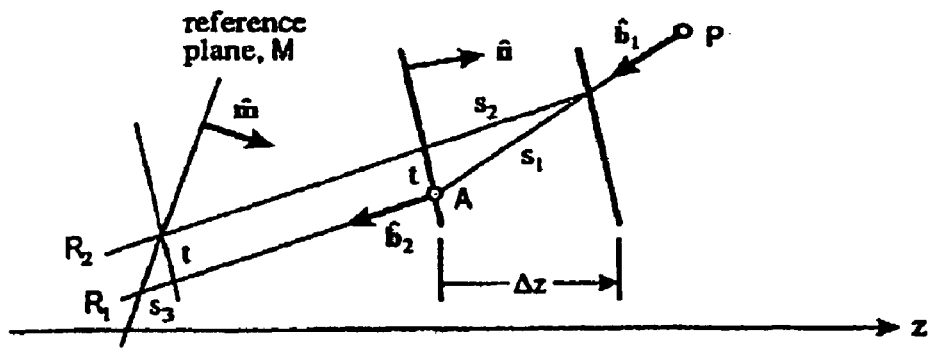
FIG. 14 is a diagram illustrating calculation of raytrace parameters for determining optical path difference.

Calculating a Wavefront Aberration from Topographic Data and Corresponding Treatment As discussed above, ORBSCAN II topography data can be used to both calculate a wavefront and to develop a course-of-treatment. One technique to achieve this is ray tracing, as illustrated in FIGS. 12–14. A corrective corneal ablation pattern can be determined from the geometry of the ocular refractive surfaces and the indices of the media separating them. This is conveniently done by finding the optical wavefront required for stigmatic imaging via reverse ray-tracing. For example, suppose the corrected system is to form a diffraction limited image on some known image plane (the retina, for example). With reference to FIG. 12, a point source is theoretically placed at the intended image, location F. Rays emanating from this source are raytraced out of the system (i.e., in the negative z-direction or from right to left in the figure), first through the modeled lens and then through the measured cornea. If the optical system is diffraction-limited with a focal point at F, then the exiting wavefront M will be planar, and the exiting rays will be mutually parallel (as they are all perpendicular to the planar wavefront).

Optical path difference (OPD): When the exiting wavefront is not planar, the corrective ablation is calculated so as to make the exiting wavefront planar. To do this, the optical path length $\phi(x, y)$ of each ray is first calculated from the source point F to a reference plane M external to the anterior cornea and oriented perpendicular to the intended line of sight. Optical path length, which is proportional to the time it takes for light to propagate from F to M, equals $$\phi(x, y) = \int_{ray\ path} n(s)\,ds \qquad (1)$$

where s is the arc length measured along the ray and n(s) is the media refractive index. Ray coordinates (x, y) are defined by the ray intersection with the external reference plane. FIG. 13 illustrates a section through the optical path length function for both a myopic and a hyperopic eye. Optical path length is always positive. The purpose of ablative correction is to flatten the wavefront (by $-\Delta\phi$) in a central area by physically flattening the front surface of the cornea (by $\Delta z$). If corneal material is to be removed in the process, then the optical path difference (OPD) from the desired planar to actual wavefront, $\Delta\phi$, must always be positive. Given that $\phi_P$ defines a plano wavefront, $$\Delta\phi = \phi(x,y) - \phi_P(x,y) \qquad (2)$$

Invariant ray model: Now how must the cornea be ablated to reduce its OPD to zero? A crude estimate of the OPD reduction can be made assuming the ray path is unchanged by the ablation. Then ablating the cornea a distance $s_1$ along a ray effectively replaces the corneal refractive index ($n_C$=1.376) with the index for air ($n_A$=1.000). To be useful, the ablated length along the ray must be translated into an ablation depth in the z-direction, which is accomplished by the eta-factor $\eta_1$, defined below (the form of $\eta_1$ is derived in the next section). Given this, the ablation depth for the invariant ray model is $$\Delta z = \frac{\Delta \phi}{(n_C - n_A)\eta_1}, \text{ where } \eta_1 \equiv \frac{s_1}{\Delta z} = -\frac{\hat{z} \cdot \hat{n}}{\hat{b}_1 \cdot \hat{n}}$$

As z is directed positive into the eye, removing corneal material always requires a positive ablation depth, $\Delta z$.

Planar neighborhood model: The next best approximation of the ablated OPD assumes the corneal surface is planar in a small neighborhood surrounding the refracting ray, and that corneal surface orientation is unchanged by the ablation. In this case, the air paths of the pre-op ray $R_1$ and the post-op ray $R_2$ are parallel, but displaced as shown in FIG. 14. The OPD between rays $R_1$, and $R_2$ depends only on the refractive indices of the two media and the distances $s_1$, $s_2$, and $s_3$. The final solution will be linear, because these three distances are all linearly proportional to $\Delta z$:

$$\Delta \phi = \phi(R_1) - \phi(R_2) = n_C s_1 + n_A (s_3 - s_2)$$

Since OPD is directly proportional to the surface displacement $\Delta z$, define a set of eta-factors as follows:

$$\frac{\Delta \phi}{\Delta z} = n_C \eta_1 + n_A (\eta_3 - \eta_2),$$

where $$\eta_j \equiv \frac{s_j}{\Delta z}, \quad j = 1, 2, 3$$

To calculate the eta-factors, define the ray vectors $S_1$ and $S_2$, and the surface tangent vector T that connects them. In the following, $\hat{b}_1$ and $\hat{b}_2$ are the unit-length direction vectors of the rectilinear portions of the ray refracted at the posterior corneal point P and the anterior corneal point A, respectively.

$$S_1 = s_1 \hat{b}_1, \; S_2 = s_2 \hat{b}_2, \; S_2 = S_1 + T, \; t = |T|$$

The perpendicular displacement of the refracting surface $\delta$ is proportional to $S_1$, $S_2$, and $\Delta z$. In the following, notice that $\hat{n}$ is the unit surface normal (positive in the z-direction) of the refracting surface, and that $\hat{z} = (0, 0, 1)$ is the unit vector defining the z-direction of the coordinate frame.

$$\delta = \Delta z(\hat{z} \cdot \hat{n}) = -S_1 \cdot \hat{n} = -S_2 \cdot \hat{n}$$

These relations can be solved for the eta-factors $\eta_1$ and $\eta_2$:

$$\eta_1 \equiv \frac{s_1}{\Delta z} = -\frac{\hat{z} \cdot \hat{n}}{\hat{b}_1 \cdot \hat{n}} \quad \eta_2 \equiv \frac{s_2}{\Delta z} = -\frac{\hat{z} \cdot \hat{n}}{\hat{b}_2 \cdot \hat{n}}$$

To calculate the final eta-factor, define the $S_3$ ray vector, and notice that $S_3 - T$ lies in the reference plane M and is therefore perpendicular to the surface normal vector $\hat{m}$ of the reference plane. (In the typical situation, the reference plane is oriented perpendicular to the z-axis and thus $\hat{m} = \hat{z}$. Nevertheless, we solve for the general case.)

$$S_3 = s_3 \hat{b}_2, \; (S_3 - T) \cdot \hat{m} = 0$$

Solving for $s_3$ we find $$\beta \equiv \frac{\hat{b}_1 \cdot \hat{m}}{\hat{b}_2 \cdot \hat{m}} = \frac{s_2 - s_3}{s_1} = \frac{\eta_2 - \eta_3}{\eta_1}$$

Finally substitution into the OPD formula gives $$\Delta z = \frac{\Delta \phi}{(n_C - \beta n_A)\eta_1} \quad (3)$$

This solution differs from the previous one by the inclusion of the beta-factor, $\beta$, which is near one. This correction is very cost-effective as the beta-factor is a simple function of the ray vector directions, which were calculated during the initial raytrace. The next higher approximation, which would account for the local curvature of the corneal surface, would be more costly. Moreover, as the ablation displaces the refracted ray by a finite amount it becomes difficult in principle to calculate the exact result by analytical means.

Iterative solution: Therefore, at a certain point iterative solutions are needed. It makes sense to use the planar model result in an iterative recalculation of the raytrace solution. The following procedure differentiates between physical OPD, which is measured with respect to the plano wavefront $\phi_P$, and iterative OPD, which is measured with respect to the iterative-goal wavefront $\phi_G$. Iterative OPD is only used temporarily during the iterative process. Only physical OPD has real physical significance.

Initial Steps

1. Given the initial anterior surface $z_I(x, y)$ and all other surfaces (both measured and modeled), reverse raytrace from F to M and calculate the initial optical path length function of the eye, $\phi_I(x, y)$, using equation 1.
2. Construct the optical path length surface for the iteration goal, $\phi_G(x, y)$. This surface is centrally plano (i.e., $\phi_G$ is identical to $\phi_P$ centrally), but may curve peripherally into $\phi_I(x, y)$ to provide for a smooth transition zone. Alternately, the transition zone can be calculated later on the iteration-goal ablation surface $z_G(x, y)$.
3. Calculate the initial iterative OPD with respect to the iteration goal, which must be positive for a realizable ablation: $\Delta \phi_I(x,y) = \phi_I(x,y) - \phi_G(x,y)$.

Iterative Steps

1. Calculate the approximate ablation depth $\Delta z$ using equation 3.
2. Mathematically fit the new anterior surface to $z(x, y) + \Delta z(x, y)$.
3. Discontinue the iteration when $\Delta z$ is small for all $(x, y)$.
4. Recalculate the final portion of the reverse raytrace from P to M, and calculate the new optical path length $\phi(x, y)$ using equation 1.
5. Calculate the corrective OPD with respect to the iteration goal (notice that the corrective OPD may be positive or negative): $\Delta \phi(x,y) = \phi(x,y) - \phi_G(x,y)$.

Final Steps

1. When necessary, make a smooth transition (with minimum variation of curvature) in the iteration-goal ablation surface $z_G(x,y)$. The result is the final ablation surface, $z_F(x,y)$.

2. Calculate the final ablation depth, which can never be negative: $\Delta z_F(x,y) = z_F(x,y) - Z_I(x,y)$
3. Recalculate the final portion of the reverse raytrace from P to M, and calculate the final optical path length $\phi_F(x,y)$ using equation 1.
4. Calculate the final uncorrected OPD with respect to the perfect piano wavefront: $\Delta\phi_F(x,y) = \phi_F(x,y) - \phi_P(x,y)$.

This approach is illustrative, and other techniques could be used.

Wavefront Sensor

Figure 5:
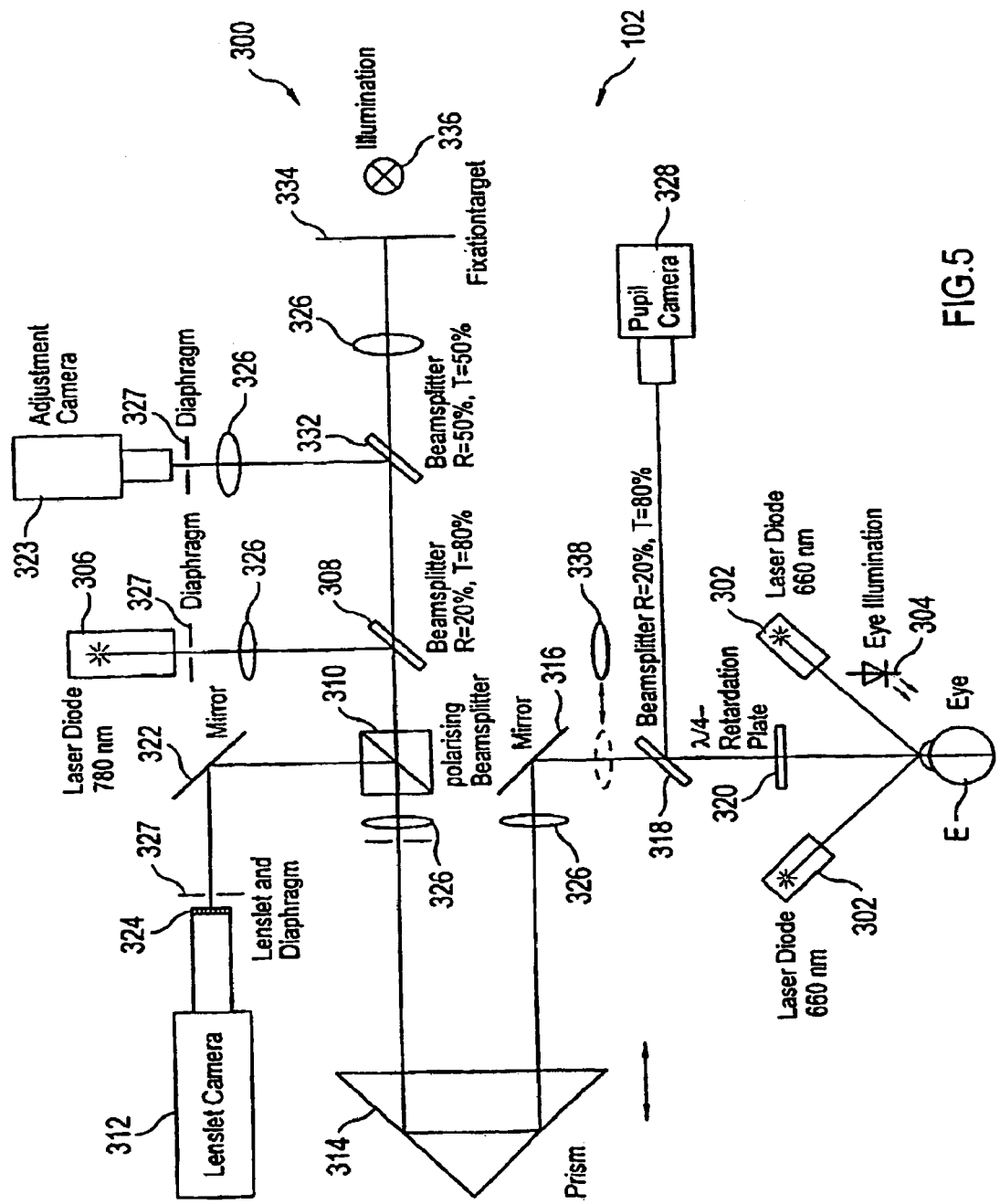
FIG. 5 is a block diagram of a preferred wavefront sensor for use in a system according to the invention.

Turning to FIG. 5, a block diagram of a preferred wavefront sensor 300 is illustrated. The wavefront sensor 300 is similar in concept to the wavefront sensor of Williams, but includes certain features that make it especially useful for receiving iris data and for sharpening the focus of light spots on a sensor used in determining the wavefront aberrations of the eye. In general, the wavefront sensor 300 focuses or scans a light (typically a laser) on the retina of an eye and then analyzes the light returned (i.e., backscattered from the retina) through the lens and corneal optics of the eye and imaged by a lenslet array. Based on optical aberrations in the eye's optics, the system develops an overall wavefront aberration analysis from the returned light. Generally, to perform the analysis, the returned light becomes aerial images formed by a lenslet camera on a sensor of the lenslet camera. From these images, the wavefront sensor develops a wavefront aberration map of what corrections are necessary to the eye's optics that would yield emmetropic, or very nearly emmetropic, vision.

To properly orient the patient's eye E, two 660-nanometer laser diodes 302, shown in FIG. 5, can be aligned at angles to the eye E. When spots on the patient's eye E from the laser diodes 302 are merged into a single spot, by appropriate adjustment of the wavefront sensor 300 (or 102), the output beams of the laser diodes 302 (or optics directing these beams), the patient, or otherwise, the eye E is positioned at, or approximately at, a precise focal distance from the wavefront sensor 300 (or 102). Alternatively, the patient's eye E can be properly oriented by a physician, technician, or other healthcare worker by visually looking at an iris image of the eye E to find the correct focal distance from the wavefront sensor 300 to reduce the overall exposure on the eye E. In this case, there is no need for the laser diodes 302. A light source, eye illumination 304, provides light for a pupil camera 328 discussed below.

Once the eye E is properly aligned, it receives light from a light source 306 (e.g., a laser diode, such as a 780-nanometer output laser diode) along an optical path to the eye E. Preferably, the laser diode 306 has more than one output power setting (i.e., two-power or multi-power modes), at least one at lower power for alignment and initial focusing and at least one at higher power for creation of a multi-spot image in a sensor (e.g., a lenslet camera) 312 discussed below. For example, typical lower and higher powers are 0.5 μW and 30 μW, respectively. These powers depend upon a number of factors, such as how long the laser diode 306 is to remain turned on at higher power.

A portion of the beam from the laser diode 306 first reflects from a beamsplitter 308 (e.g., 80% transmittance, 20% reflectance). The reflected beam passes through a polarizing beamsplitter 310, which ultimately improves the signal to noise ratio (or signal intensity) of light backscattered from the retina of the eye that is eventually detected by the lenslet camera 312, as discussed below. The beamsplitter 310 polarizes the light received from the laser diode 306, generally passing light linearly polarized along one direction and reflecting light not polarized in that direction. The polarized light is then passed through a trombone-type prism 314 which is used to adjust the focus of the light from the laser diode 306 onto the retina of the eye E, at which point light backscattered onto the lenslet array from the light impinging on the retina will also be correctly or nearly correctly focused. Alternatively, other optical focusing arrangements as understood by one skilled in the art are possible. The light from the trombone prism 314 is reflected from a mirror 316, passed through a beamsplitter 318 (e.g., 20% reflectance, 80% transmittance), and then through a λ/4 waveplate 320. The λ/4 waveplate 320 is oriented to produce substantially circularly polarized light from the linearly polarized light. The significance of this will be appreciated in the discussion below of backscattered light returned (the "returned light") from the eye E to the polarizing beamsplitter 310.

After passing through the λ/4 waveplate 320, the light is then focused onto the retina of the eye E. The light is backscattered or reflected from the retina and the backscattered light spot on the retina then passes back through the optical components of the eye E, such as the lens and the cornea. On the return path, the circularly polarized image light is retarded again by the waveplate 320 to yield light linearly polarized perpendicular to the incoming linearly polarized light formed on first passage through the waveplate 320, as discussed above. A portion of the perpendicularly polarized light then passes through the beamsplitter 318, reflects from the mirror 316, passes back through the prism 314, and returns to the polarizing beamsplitter 310. At this point, all or most of the light is perpendicularly polarized, and is thus substantially reflected by the polarizing beamsplitter 310 and then reflected by a mirror 322 into the lenslet-imaging camera 312. To get some of the returned light into an adjustment camera 323, discussed further below, the waveplate 320 can be tilted and/or rotated from its optimal orientation (e.g., rotated by approximately 5 degrees). In this implementation, the light received by the adjustment camera 323 would have a polarization substantially perpendicular to the returned light. Other schemes besides tilting or rotating the waveplate 320 from its optimal orientation for providing returned light to the adjustment camera 323, including changes to the optical path and optical components of the wavefront sensor 300 (or 102), are envisioned and are included within the scope of the present invention. For example, the mirror 322 instead could be a device having a controllable transmittance and reflectance, such as a liquid crystal device, and the adjustment camera and any focusing optics can be positioned to receive a fraction of the returned light that is transmitted by the controllable device. In such an implementation, the beamsplitter 308 would be unnecessary and the light received by the controllable device would have substantially the same or parallel polarization as the polarization of the returned light.

The lenslet camera 312 is preferably a charged couple device (CCD) camera, such as a TM-9701 manufactured by Pulnix, which includes an array of lenslets 324, although other types of cameras and other sampling optics analogous to the lenslet array 324 (including optics separate from a camera) could be used. For example, an ICX 039DLA camera by Sony Corporation can be used for both the lenslet camera 312 and the pupil camera 328. The lenslet array 324 forms aerial images on the light sensing element (e.g., CCD array) of the lenslet camera 312 from the returned light reflected by the mirror 322. The waveplate 320 can help to reduce the amount of unwanted backscattered or stray light to improve the signal intensity or the contrast of the aerial images. The lenslet array 324 focuses portions of the light that has initially passed through the optical components of the eye E so that the refractive wavefront aberration effects of the eye E can be determined, similar to what is disclosed in Williams. In this regard, once the wavefront aberrations, and thus phase error, of the eye E have been determined, they can be transformed to a required ablation profile for removal of corneal tissue to correct or improve vision by taking appropriate account of parameters of the eye E (e.g., the refractive indices of eye E components, and/or other parameters). One technique for determining an appropriate profile is to simply scale the wavefront data such that the scaled data generally corresponds to the amount of tissue needed to be removed from the patient's cornea. Laser systems can then remove that profile of tissue from the cornea. Marks on the eye E can be employed to aid in aligning the eye E during acquisition of wavefront sensor data.

Preferably, the lenslet array 324 is an array of approximately 25×25 lenslets, each 600 square microns, such as a 0600-40-S manufactured by Adaptive Optics Associates, Incorporated. This lenslet size is smaller than the lenslet size described in the aforementioned U.S. Pat. No. 5,777,719 patent and in other systems, and is made possible because of the enhanced intensity of light to the lenslet camera 312 provided by components of the wavefront sensor 300 to be discussed below. The optical path of the wavefront sensor 300 shown in FIG. 5 can also include lenses 326 (e.g., four lenses) and diaphragms or apertures 327 (to allow changes in beam sizes) that are typical of illumination, imaging, and focusing optics, and which also can represent other possible optical components omitted for clarity. For example, in one embodiment of the invention, the focal length of one or both of the lenses 326 about the trombone focusing prism 314 can be changed, perhaps shortened, to accommodate a smaller beam width entering the lenslet array 324. In another embodiment, the range of possible dioptric measurements that can be made with the wavefront sensor 300 (or 102) can be changed, for example, with appropriate selection of the lens 326 in front of the laser 306, to adjust for the natural distribution of poor eyesight in the general or a select population of patients. One way to do this is to position the lens 326 (e.g., a −5 diopter lens) in front of the laser diode 306 such that the laser beam is no longer parallel. This provides a certain offset in diopters that can be used to test the patient's eye with the wavefront sensor 300 (or 102). In a nonlimiting example, the dioptric range can be modified from a symmetrical −8 to +8 diopters with a symmetrical design to an asymmetrical −13 to +3 diopters with an asymmetrical design, as will be appreciated by those skilled in the art. This can be done without changing the size of the trombone focusing prism 314 (or other tuning device) and/or parameters of the optics.

Alternatively to the position of the lens 326, a lens 338 could be moved into the path to the lenslet camera 312. A number of locations within the path to the lenslet camera 312 can be employed to adjust the overall range of the captured wavefront sensor 300. It will be appreciated that by employing either the lens 326 or 338 moveable into and out of position, the length of "throw" necessary for the trombone is reduced. Further, the laser diode 306 typically will have some inherent "astigmatism" of its own. This can be aligned with astigmatism typically found in a patient's eye E, again increasing the overall range of the wavefront sensor 300. Specifically, such astigmatism is aligned "with the rule" as typical patient's astigmatism is found, and the lenslet camera 312 and corresponding wavefront sensor 300 software can take into account this inherent astigmatism as providing an even greater range of determinable astigmatism.

A pupil camera 328 is shown receiving (e.g., 20% of) the reflected light from the beamsplitter 318. The pupil camera 328 preferably provides the iris image data 132 for the iris image 136 via a control system (not shown) similar to or the same as the control system 156 discussed below in the discussion of alignment techniques. To compare, data from the lenslet camera 312 is processed and ultimately provided as the aberration data.

The pupil camera 328 is placed in the optical path between the eye E and the trombone focusing prism 314, which allows the pupil camera 328 to focus on the pupil and iris of the eye E, irrespective of changes in the focal length of the remainder of the system for focusing on the retina. Thus, the pupil camera 328 can develop a clear image of the surface of the eye E independent of the depth of the eye E and the corresponding distance from the retina to the iris.

Focus Adjustment Camera

The wavefront sensor 300 also includes the alignment or adjustment camera 323 that receives an image of the backscattered spot on the retina of the eye E from a beamsplitter 332 (e.g., 50% reflectance, 50% transmittance). The adjustment camera 323 is in the path of the optics that focus light on the retina of the eye E and is independent of the lenslet camera 312. The adjustment camera 323 makes it possible to precisely determine when the light spot impinging from the laser diode 306 onto the retina is in, or approximately in, focus, and thus aids in determining when the backscattered light from the retina is in, or approximately in, focus on the lenslet camera 312. With the adjustment camera 323, the spot of light on the retina can be seen, which is the ultimate source for the centroids signal (as in Williams), and can be automatically examined for when it is in sharpest focus to aid in focusing the aerial images on the lenslet camera 312 as sharply as possible. In previous systems, no adjustment camera was provided. Such systems would rely just on a lenslet camera to aid in focusing light on a retina and backscattered light on the lenslet camera. The problem with this approach is that the portion of the wavefront sampled by an individual lenslet of an n-lenslet array forms individual spots on the camera's sensor with at most approximately 1/n of the total energy (or power) of the returned backscattered light just before entering the lenslet camera. As a result, the retina (or eye) was exposed to light energy (or power) that was maintained high unnecessarily. As can be appreciated by those skilled in the art, with the present invention, the overall exposure of the retina (or eye) can be reduced relative to these previous systems because the light energy (or power) received at the adjustment camera 323 need only approximate the light energy (or power) received at an individual lenslet of the lenslet array. The adjustment camera 323 is used to directly observe the focusing of light on the retina from the laser diode 306 while the laser diode 306 is in its lower power mode. The adjustment camera 323, as implemented, thus aids focusing the aerial images on the lenslet camera 312 as sharply as possible while the laser diode 306 is in its lower power mode as well. In so doing, account can be taken of the transmittances of the polarizing beamsplitter 310 and the beamsplitter 308, the reflectance of the beamsplitter 332, and any tilt or rotation that is introduced to the λ/4 waveplate 320 from its optimal orientation to allow a portion of the returned light to pass back to the adjustment camera 323.

As discussed above, the adjustment camera 323 is used to make sure that the spot on the retina is as sharp as possible.

This means that the correct trombone 314 settings are checked as well as patient alignment. A signal can be developed (e.g., from the adjustment camera or from a control system, such as the control system 156 in FIG. 7C) from these settings and alignment for a manual check or for an automatic start of patient measurements or examination. Such operation also allows for enhanced light intensity into the lenslet camera 312 only for the period of time that measurements or examination occurs, and not during the focusing and adjustment period discussed above.

In the lower power mode the laser diode 306 is placed at a power low enough to prevent damage to the retina of the eye E, such as 0.5 µW. The control system's use of the adjustment camera 323 to aid in focusing the laser diode 306 onto the retina can be accomplished in many ways. For example, the spot size on the retina can be minimized or the intensity of the spot on the retina can be maximized by adjusting the position of the trombone prism 314 in the optical path of the captured wavefront sensor 102 until the spot is as small as possible. The position of the trombone prism 314 establishes a "base line" myopic or hyperopic degree of dioptric correction necessary to initially compensate for the lower order refractive optical aberration characteristics of the eye E. Making sure that the lasers 302 are aligned at an angle that maintains an overlap of their respective spots on the retina (or other method such as manually, or by visual examination of, aligning the patient's eye) with the laser diode 306 in conjunction with adjusting the position of the trombone prism 314 is helpful while determining the base line level of myopic or hyperopic error or correction.

Once focusing is achieved, the laser diode 306 is placed in the higher power mode for a very short period of time. For example, it may be possible to use a power of 30 µW in a spot size of 10–20 microns on the retina for a period of 400 msec. Although higher intensity could damage the retina if maintained for a prolonged period of time (e.g., more than 100 sec), such a short burst is harmless. The short burst does, however, greatly increase the intensity of the individual spots on the sensor of the lenslet camera 312, so the combination of the multi-powered laser diode 306, the adjustment camera 323, the lenslet array 342, and the lenslet camera 312 can allow for higher signal intensity or higher contrast lenslet images to be developed by the lenslet camera 312 than in other systems. The higher power laser diode 306 mode may allow the use of smaller individual cross-sectional area lenslets in the lenslet array 324 compared to other systems.

Once the lenslet camera 312 data is provided, it can be directly used via the Zernike polynomials to create the wavefront aberration data, or the wavefront aberration data can be calculated as the average of a series of exposures. For example, the system can employ five "shots" and then average either the captured data or average the corresponding Zernike data. Further, widely diverging "shots" can be discarded. In the disclosed system, preferably five "shots" are taken, and the wavefront aberration data determined as the average calculated wavefront aberration.

It will be appreciated by those skilled in the art having the benefit of this disclosure that various types of components can be used to substitute for components implemented in the wavefront sensor 300 and various optical configurations are possible to form other embodiments of the invention. For example, a high intensity, collimated light source, or multiple light sources, for example, one low power and one high power, can replace the laser diode 306. The adjustment camera 323 can instead be placed in the path of the mirror 322, and the lenslet array 324 of the lenslet camera 312 can have more or fewer lenslets, as desired or according to design. Further, it will be appreciated by those skilled in the art that all of these components are generally controlled by a control system, such as a microcomputer. A wide variety of other configurations are possible that are within the scope and spirit of the present invention.

Practice of this invention requires alignment of information from various diagnostic measurements and also with the ablation profile delivered by the laser to the eye. Various techniques are known in the art for achieving such alignment and any may be used in the practice of this invention. However, alignment techniques using an image of the iris of the eye (or a portion of the iris or other identifying eye features) are currently preferred.

Use of Iris Data to Align Laser Treatment

Figure 6:
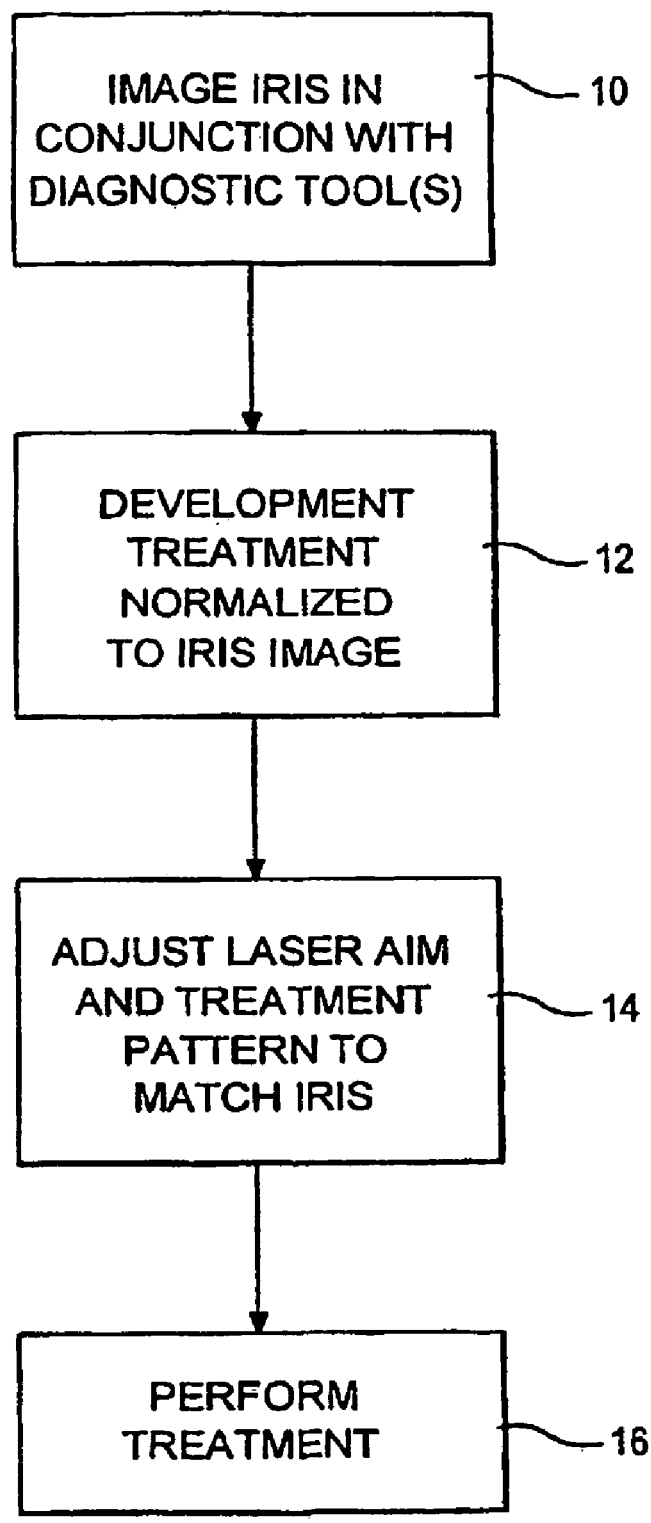
FIG. 6 is a flow diagram illustrating the acquisition of iris image data and the use of the data for a subsequent laser treatment.

FIG. 6 shows the general flow of a method of using a system implemented according to an embodiment of the invention. At block 10, the iris is imaged in conjunction with acquiring refractive data using a diagnostic tool. This imaging and the use of the diagnostic tool can take many forms. For example, the tool can be used well in advance of the laser treatment, such as using a corneal surface topography system to determine a corneal or refractive profile. Or it can be used immediately before refractive surgery. In any case, the imaged iris or some representation of the iris is maintained with the data developed by the diagnostic tool.

Proceeding to block 12, a treatment is then developed based on the data provided by the diagnostic tool. For example, this treatment may treat for a certain degree of myopia and an irregular astigmatism. This treatment can be, for example, a treatment developed using the algorithms of PCT/EP95/04028, entitled "Excimer Laser System for Correction of Vision with Reduced Thermal Effects," published Apr. 25, 1996, which provides a dithering algorithm to modify a corneal profile, in conjunction with the distributed system of U.S. Pat. No. 5,891,132, entitled "Distributed Excimer Laser Surgery System," issued Apr. 6, 1999. This treatment, however, is normalized to the stored representation of the iris image. By doing so, subsequent modifications to the treatment based on additional diagnostic tool data can be normalized to subsequent iris images.

Further, the treatment itself is preferably aligned to the iris of the patient. This is done at block 14, where the laser aim and the treatment pattern are normalized to the image of an iris of the patient under treatment. This normalization can take very general forms, such as a translation of the aim of the laser to an appropriate point, or more sophisticated forms, such as by rotation or even scaling and skewing of the treatment to match the iris image that is presented to the laser system.

Proceeding to block 16, the laser treatment is then performed. Of note, during the laser treatment the system can periodically or even continuously match the iris data to the stored representation of the iris data, in essence tracking the patient's eye.

Figure 7A:
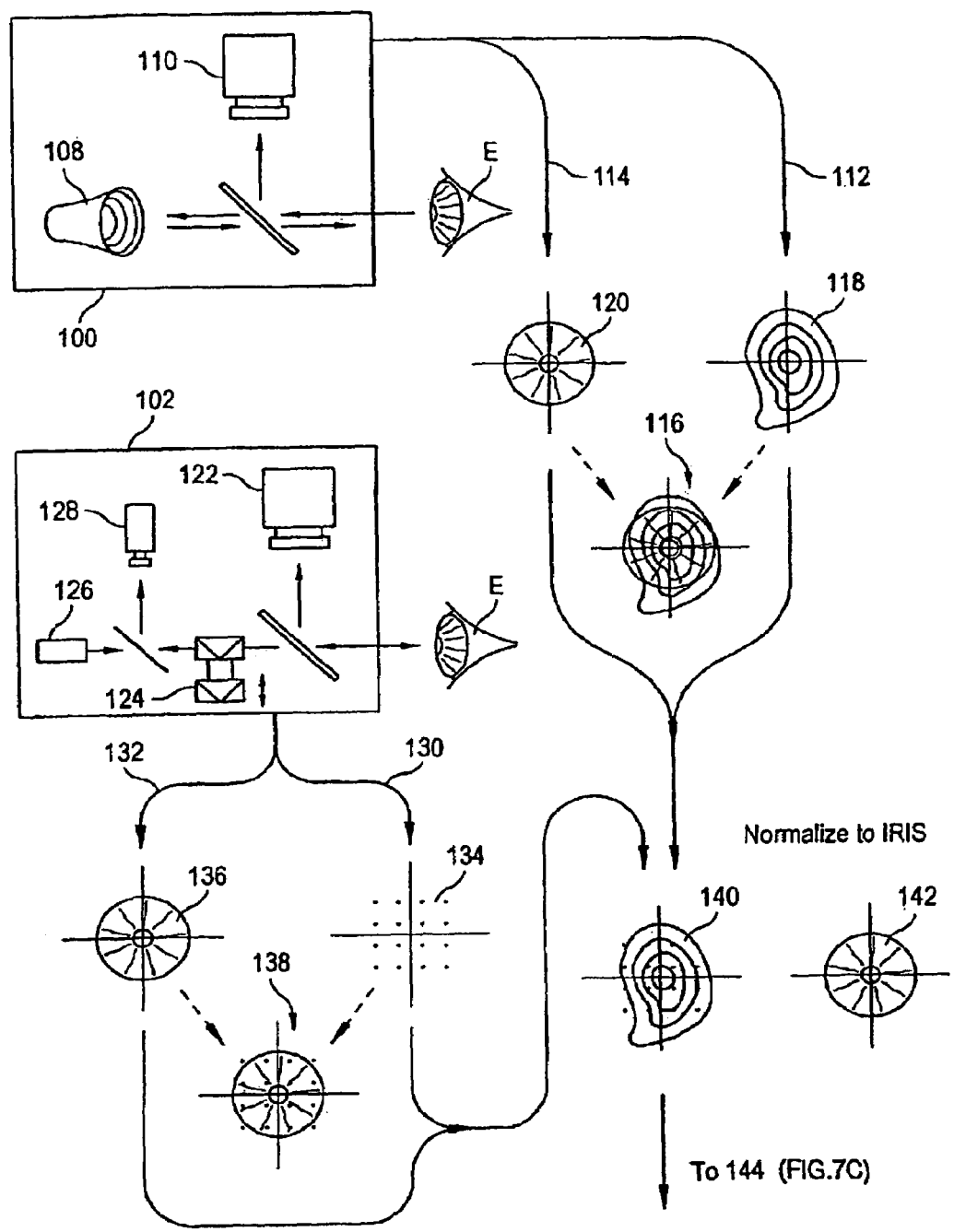
FIGS. 7A, 7B, and 7C are block flow diagrams illustrating the acquisition of iris data in conjunction with refractive characteristic data, the generation of a treatment based on that data, and the use of that treatment data in conjunction with an iris image to perform laser surgery.
Figure 7B:
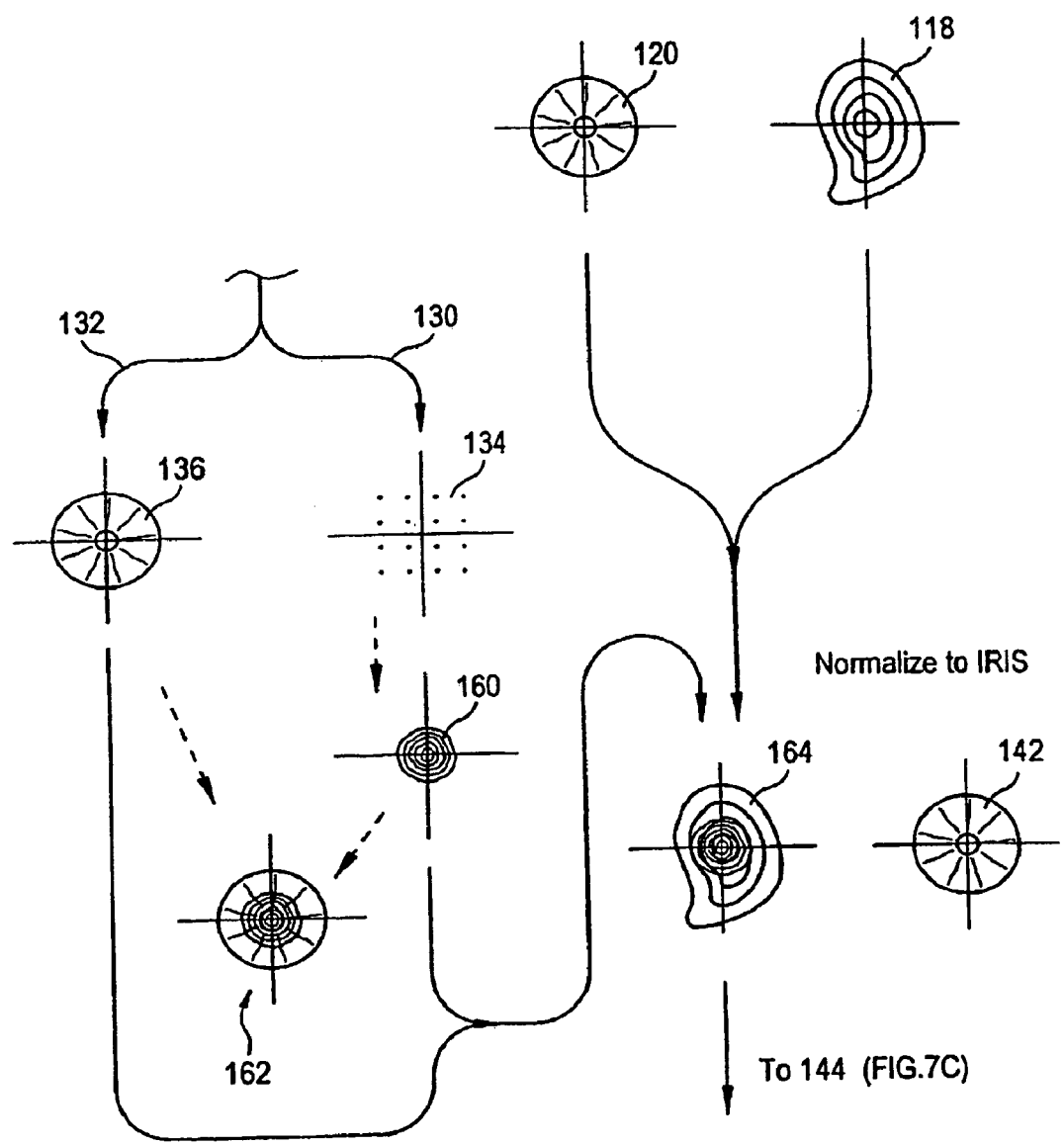
Figure 7C:
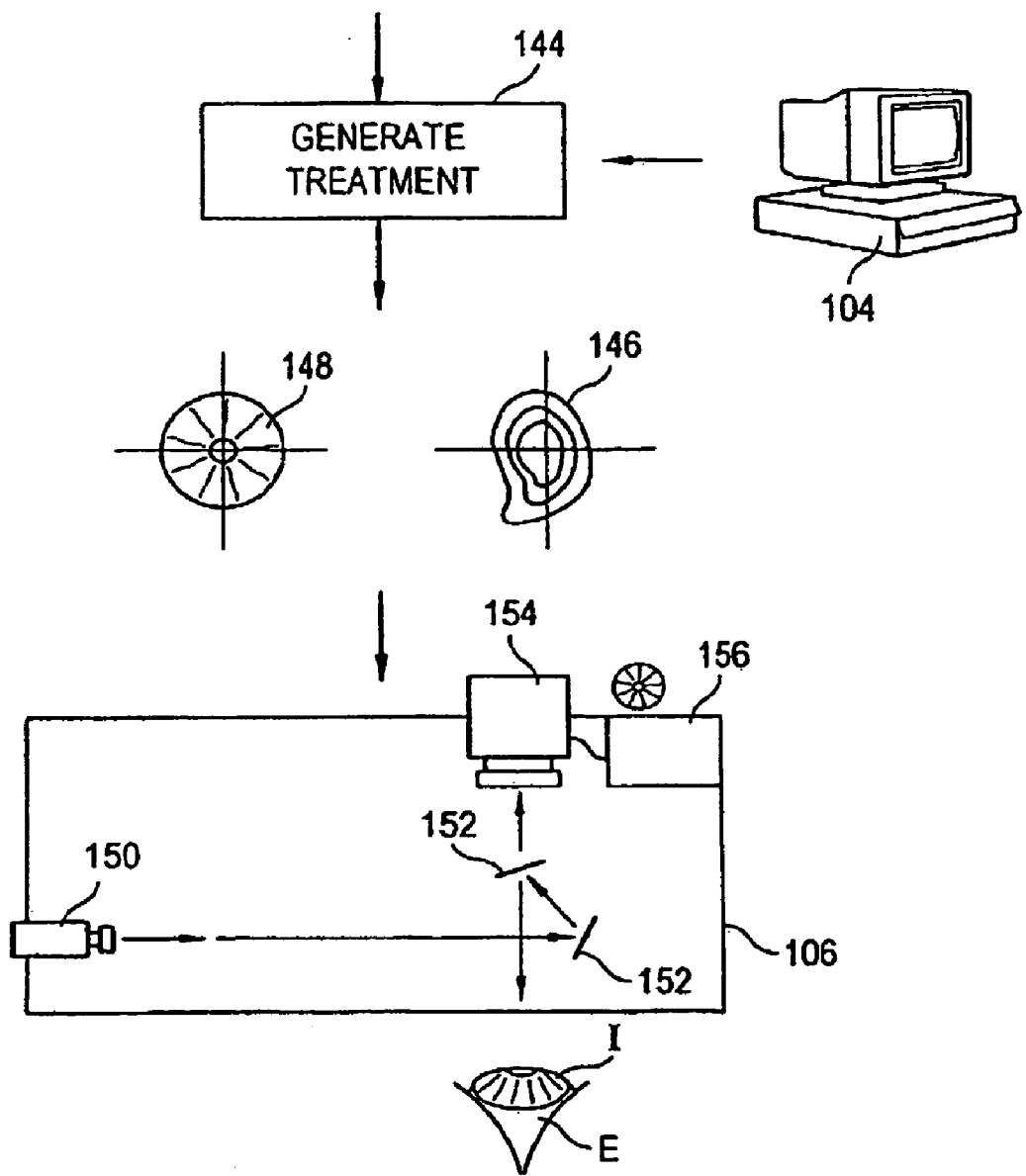

Turning to FIGS. 7A, 7B, and 7C, the general flow of determining refractive data, normalizing to the iris image, generating a course of treatment, and then applying a course of treatment is shown in a system according to the invention. In accordance with this invention, refractive characteristics of an eye to be treated are determined by a corneal surface topography system 100 and a wavefront sensor 102. Both of these devices generally provide data indicative of refractive characteristics of the eye. In addition, a computer workstation or computational unit 104 is shown that is used to create a customized course of treatment based on the data provided by the diagnostic tool. Although shown as a separate workstation 104, such as for use in a distributed system like that disclosed in PCT/EP97/02821, the workstation 104 and/or its functionality could be incorporated within many of the other components of the system of FIGS. 7A, 7B, and 7C. For example, also shown in FIG. 7C is a laser system 106, which receives both the treatment generated by the workstation 104 and corresponding iris data. The laser system 106 could incorporate the functionality of the workstation 104, generating an appropriate laser treatment within the laser system 106 itself.

Beginning in FIG. 7A, the corneal topography system 100 gathers corneal topographic data from a patient's eye E. The illustrated topography system includes Placido disk-type hardware 108 as well as a pupil or iris camera 110. These components are known to the art, and a variety of techniques are known to produce corneal topographic data. For example, the System 2000 by EyeSys produces corneal topographic data, and ORBSCAN II® topography by Orbtek produces not only surface corneal topography, but also overall topography for the various components of the eye. The former system is a Placido disk based system; the latter is an automated slit lamp system. The ORBSCAN II® system uses surface elevations and ray tracing to determine refractive errors of the eye. The topographic system 100 typically can produce data output 112 in a variety of formats and gathered using a variety of techniques, such as absolute corneal height at a variety of points, corneal curvature at a variety of points, and the like.

Besides the corneal data 112, the corneal topography system 100 also acquires a corresponding "snapshot" of the visible surface of the eye E, providing first iris (and pupil) image data 114 representative of an iris (and pupil) image 120. Many corneal surface topography systems have a pupil camera that can acquire this image. As is further discussed below, the pupil or iris camera 110 can provide the iris image data 114 in a variety of formats, such as a standard image format, or as a reduced format in which various iris or pupil artifacts are identified. Such artifacts can include those identifiable along the edge of the interface of the pupil and iris. The iris data 114 can be some combination of image and recognized artifacts of the iris, the pupil, their interface, or other eye structures as well.

The pupil or iris camera 110 can be a variety of camera types, such as a visible light, infrared, or other camera suitable to capture the iris image 120. Preferably, the image is acquired at the same time that the topography components (Placido disk-type hardware) 108 are gathering the topography data 112, although before or after would also be acceptable.

As illustrated in FIG. 7A, the topography data 112 and the iris image data 114 are preferably related according to some coordinate system, as represented by overlaid images 116. The relationship between a determined topography 118 and the iris image 120 is maintained in the data.

As discussed below, the iris image data 114 for the iris image 120 is useful for aligning a surgical tool (here, the laser system 106). The data 114, however, is also useful for normalizing data from various other ophthalmic diagnostic instruments. Specifically, the wavefront sensor 102 also analyzes the refractive irregularities or aberrations in the eye E. In the wavefront sensor 102, preferably a pupil camera 122 is focused onto the eye E in front of certain "trombone" optics 124. The trombone optics 124 (e.g., a focus or optical path adjusting tuning device or optics) is used to change the optical path length and focus a laser 126 onto the retina of the eye E. The trombone optics 124 can be used to determine and compensate for the low order aberrations of the eye E, such as defocus. In one embodiment, the wavefront sensor 102 gathers data for determining optical aberrations in the eye E via a lenslet camera 128. As discussed above, a variety of other wavefront sensors or other type of systems for determining refractive ophthalmic wavefront aberrations can be employed.

As with the corneal surface topography system 100, the wavefront sensor 102 preferably provides aberration data 130 and iris (and pupil) image data 132 from the pupil camera 122. These data establish an aberration profile 13—e.g., a wavefront sensor spot profile, from which centroids of the spots are determined in determining the wavefront aberrations of the eye, as in Williams—and an iris (and pupil) image 136. The iris image data 132 can be similar to the iris image data 114. The wavefront sensor data 130 and the iris image data 132 also are normalized to each other, as illustrated by an overlapping reference frame 138 in FIG. 7A. The pupil can be dilated when the aberration data 130 and the image data are acquired, or can be left undilated.

Various types of refractive data can be determined and employed in developing a course of treatment for refractive surgery, such as LASIK. These data can include corneal topographic data, wavefront sensor data, corneal thickness data or other differential profiles (e.g., using ultrasound) of eye components, and other types of refractive data developed from various sources, such as from slit-scanning or optical coherence topography techniques. For example, ultrasound can be used to measure not only corneal thickness, but also the epithelial and other eye surfaces, the amount of stromal component in a microkeratome-cut flap (for LASIK), the residual stroma under the flap, and the like. These data are typically provided on a point-by-point basis on the eye E, at varying resolutions. For example, the corneal topography data 112 from the corneal topography system 100 generally will have a higher resolution than the wavefront sensor data 130. Similarly, certain types of data are directed towards one aspect of the eye E, such as corneal surface topography data 112 mapping the surface topography of the eye E, while other data may reflect other aspects of the eye E, such as total refractive error found in the wavefront sensor data 130 from the wavefront sensor 102.

Further, the refractive diagnostic tools could be of a variety of configurations, such as a fixed, bench-type system, hand-held, or multiple systems integrated into a single tool. One skilled in the art will recognize that the techniques according to the invention can be implemented in a wide variety of actual physical embodiments.

In one embodiment of the invention, these data sets are normalized to each other for more accurate generation of a refractive treatment. Here, the topography data 112 and its corresponding iris image data 114 are normalized to the wavefront sensor data 130 and its iris image data 132. For example, these two data sets are normalized to each other (illustrated by a diagram 140) based on similarities of the iris image 120 and the iris image 136 (illustrated by an iris image 142). As discussed above, this normalization may result from an overlapping of the iris images themselves, or instead from an adjustment of characteristic elements of the iris (and pupil) images, as discussed below in conjunction with FIG. 8.

In a particular embodiment shown in FIG. 7B, the aberration profile 134 is processed (e.g., via fitting Zernike polynomials, as discussed in Williams and herein) to develop wavefront aberration data shown as a pupil wavefront aberration (e.g., contour) plot 160. The wavefront sensor data 130 and the iris image data 132 (FIG. 7A) are normalized also to each other, as illustrated by an overlapping reference frame 162 in FIG. 7B. As discussed above, the pupil is preferably dilated when the aberration data 130 and the image data are acquired, and these data sets are normalized to each other for more accurate generation of a refractive treatment. The topography data 112 and its corresponding iris image data 114 are normalized to the wavefront sensor data 130 and its iris image data 132. For example, the normalization of these data is illustrated by a (superimposed) diagram 164 based on similarities of the iris image 120 and the iris image 136 (illustrated by an iris image 142) in parallel to the discussion of FIG. 7A above. The topography data 118 extends over a larger portion of the eye, such as over most or all of the cornea, while the wavefront aberration plot (or data) 160 generally extends only over the pupil or a portion of the pupil. Some correlation between the pupil wavefront aberration contour plot 160 and the topography 118, when overlapped as in or similar to the diagram 164, may be apparent, as will be appreciated by those skilled in the art even if no iris image data are used for alignment or for normalization. For normalizing or superimposing the topography and the wavefront aberration data (e.g., the topography data 118 and the pupil wavefront aberration plot 160), suitable account may be taken of the variations in optical path length (e.g., from the wavefront aberration data) or refractive index (e.g., by averaging refractive indices) of the eye in order to correlate these data, as will be appreciated by those skilled in the art.

Whether data are generated according to the procedure outlined in FIG. 7A or in FIG. 7B, as illustrated in FIG. 7C, a computer program then generates a treatment profile 144. This can be done, for example, in a stand-alone computer 104, a computer connected to the Internet or other network, or in a computational system that is part of the laser system 106, the topography system 100, the wavefront sensor 102, or other systems. The treatment generated could be a variety of treatments. For example, an irregular treatment pattern could be performed, as illustrated in the aforementioned U.S. Pat. No. 5,891,132, or a variety of other types of treatments could be performed, including, but not limited to, a variable spot size, a scanned slit, or a fixed scanned spot size laser treatment. Regardless of the treatment performed, it is generated with respect to the data 140 or 164 from the various diagnostic tools, and can be maintained normalized to the stored iris image 142.

The data from the various diagnostic tools can be used in a variety of ways to create treatments. For example, the data 130 from the wavefront sensor 102 could be solely used to create a treatment, or, instead, the data 112 from corneal surface topography system 100 could be used. Other alternative types of refractive diagnostic tool data can similarly be used solely to create treatments. Advantageous aspects of the data from the various tools could be combined to yield better overall refractive treatments. For example, the corneal surface topography system 100 returns surface topography data regardless of the amount of dilation of the pupil, but the wavefront sensor 102 may be limited by the amount of dilation present in the pupil (i.e., the wavefront sensor 102 typically only measures refractive effects of optical elements that are in the optical path). Therefore, as illustrated by the diagram 164 in FIG. 7B, the data 112 from the corneal surface topography system 100 is employed over a surface area larger than the dilated pupil, while the data 130 from the wavefront sensor 102 is used for the central portion within the area of the pupil. In both cases, the data 130 and the data 112 can be reconciled by a first spatial normalization using their respective iris images 120 and 136.

Referring again to FIG. 7C, based on the treatment generated 144, typically, a course of treatment, such as a series of shots, a series of scanned slits at various aperture sizes, or a variety of other types of treatment, is provided for a particular type of laser system 106. The course of treatment, illustrated by a profile 146, is itself spatially referenced to data 148 representing the iris image. The data 148 again could be an image of the iris itself, a high contrast representation in black and white of the iris, a location representation of various features of the iris, or a variety of other representations of the iris. In general, the data 148 representation of the iris should be suitable to allow the course of treatment 146 to be aligned with the actual iris of the eye E when the eye E is to be treated by the laser system 106.

The laser system 106 is then loaded with the treatment profile, including the course of treatment 146 and the iris data 148. Referring to FIG. 7C, the laser system 106 can be of a variety of types, such as a 193 nanometer excimer laser, and will typically include a laser 150, an aiming system 152 (e.g., a series of optical components used to direct light from the laser 150 to the eye E), a pupil camera 154, and a control system 156. A lower power aiming or reference beam (not shown) typically is used in conjunction with the laser 150. The aiming beam, for instance, a laser beam, can be monitored by the pupil camera 154, which is typically an infrared camera, and can be used to aim the laser 150 as described in U.S. Pat. No. 5,620,436, entitled "Method and Apparatus for Providing Precise Location of Points on the Eye," issued Apr. 15, 1997 [PCT/EP95/01287, published Oct. 19, 1995].

In operation, the pupil camera 154 provides an image of the iris I (see FIG. 7C) of the eye E to the control system 156, which controls the aiming system 152. The image of the iris I actually provided to the excimer laser system 106 is compared to the iris data 148 associated with the course of treatment 146. The aim of the laser head 150 is then adjusted such that the iris data 148 is co-aligned essentially with the image of iris I provided by the pupil camera 154. This can entail translation, rotation, scaling, skew, or a variety of other transformational functions. The translation that is applied to the iris image data 148 necessary to align it with the iris I is similarly performed on the course of treatment 146, such that the ultimate course of treatment, when it is applied, corresponds to a course of treatment necessary to reduce the optical effects as predicted in the treatment generation 144.

The data of the course of treatment 146 itself can be altered, or the aim of the laser system 106 or the rotational alignment of the patient instead can be altered. Regardless of the methodology, the iris data 148 are used to align the iris I before the treatment 146 is applied.

Various types of eye surgery can benefit from the disclosed techniques. PRK can be applied to the external surface of the eye, or a LASIK procedure can be performed by first resecting a portion of the cornea and then applying laser treatment underneath. Further, the techniques can lend themselves to other, non-keratectomy-types of treatments, such as excimer keratotomy, or various types of thermal approaches to refractive correction. These courses of treatment can be accurately aligned with the iris of the eye, such that the calculated treatment pattern is provided more precisely to theoretically optimal positions.

Other benefits flow from using the iris data associated with both the diagnostic and the treatment data. For example, when a patient is in an upright position for diagnostic evaluation, sometimes the position of the eye may rotate slightly within the eye socket compared to when the patient is in a reclining position. Similarly, the patient's head alignment can affect eye rotation even when the body stays in the same position. Although the patient's brain can compensate for a slight amount of such rotation, in a highly precise correction treatment pattern for higher order defects, the change in the rotational alignment literally can rotate the eye out of position with respect to the treatment, causing a faulty treatment to be applied to the eye. The effects of such a misalignment typically are not pronounced for fairly basic courses of treatment, such as myopia and hyperopia, and even for a minor treatment of astigmatism, but with higher order defects, such as irregular astigmatism, glare, halo, and the like, the benefits of the highly precise treatment can be lost unless precise alignment with the optimal spatial treatment position is obtained and maintained. The techniques according to the invention can reduce such loss of alignment.

With respect to the iris matching and alignment itself, a variety of techniques can be employed, either using actual images of the iris or digital representations of various features of the iris. These techniques have been employed in recognition systems based on the unique features of an iris, such as U.S. Pat. No. 5,572,596 to Wildes, et al., issued Nov. 5; 1996, entitled "Automated, Non-Invasive Iris Recognition System and Method," assigned to David Sarnoff Research Center, Inc. of Princeton, N.J., and U.S. Pat. No. 4,641,349 to Flom, et al., issued Feb. 3, 1987, entitled "Iris Recognition System," both of which are incorporated by reference herein in their entirety. The former of these patents discusses scaling, rotation, and translation; the latter of these patents discusses the various features that can be used to uniquely match and identify an iris, and also discusses that a control mechanism can be used to adjust the position of the iris relative to the camera. In an embodiment of the present invention, a similar technique additionally can be used to aim the laser system 106. Similarly, U.S. Pat. No. 5,291,560 to Daugman, issued Mar. 1, 1994 and entitled "Biometric Personal Identification System Based on Iris Analysis," assigned to Iri Scan, Inc. of Mount Laurel, N.J., also incorporated by reference herein in its entirety, further discusses the "optical fingerprint" provided by the iris. The pattern matching and feature matching techniques of these patents and otherwise known to the art are employed for alignment purposes rather than strictly identification purposes.

Alternatively, or in addition, the camera 154 of the laser system 106 can receive an image of the iris I which is then displayed on a screen. The iris image data 148 can then be superimposed to allow the physician, technician, or other healthcare worker to manually aim or adjust the laser system 106, or to manually verify the aim of the system 106.

Figure 8:
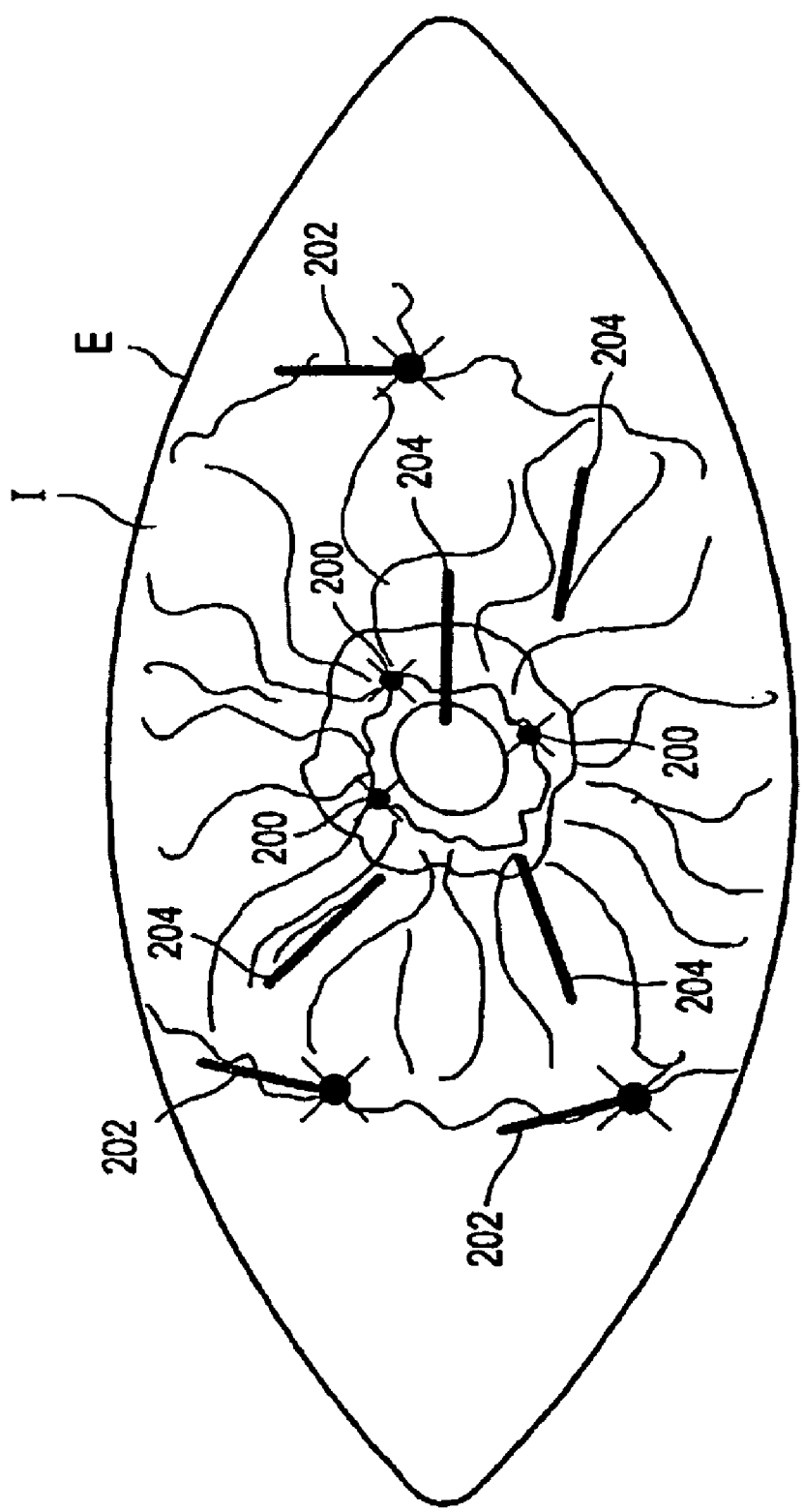
FIG. 8 is a diagram illustrating various features of an eye that can be used as characteristic iris.

Referring to FIG. 8, the iris I of the eye E is illustrated in more detail, showing how particular features can be employed for matching the patient's eye E for treatment with his or her previously stored iris I image. For example, a set of points 200, defining generally circular features such as collarattes, can be employed as descriptors, as can concentric furrows 202 or radial furrows 204. Other features that can be used are generally described in the above-referenced U.S. Pat. No. 4,641,349 to Flom, which include pigment spots, crypts, atrophic areas, tumors, and congenital filaments. Similarly, the pupil can be used in iris matching as well, for example, as a center reference point from which iris features then define the rotational position of the eye. Fewer or greater features can be employed, for example, depending on the complexity of the treatment to be applied. If the treatment is rotationally symmetrical, such as a treatment for pure myopia or hyperopia, rotational displacement is of no consequence, so the center point can be located with respect to the pupil. But with greater complexity of treatment, more detailed features can be employed for more precise registration of the eye E before treatment. Alternatively, artificial features can be imposed upon the eye E, for location, including in the iris area. For instance, three laser marks can be created on the eye E if the treatment is to occur before the laser marks would heal. Then, the diagnostic steps can be taken and the treatment followed soon thereafter. Further, other identifying portions of the visible surface of the eye can be used, apart from the iris I. In all of these techniques, features of the visible portion of the eye E are employed for registration between the diagnostic system, the developed treatment, and the actual treatment as applied to the eye E.

Figure 9:
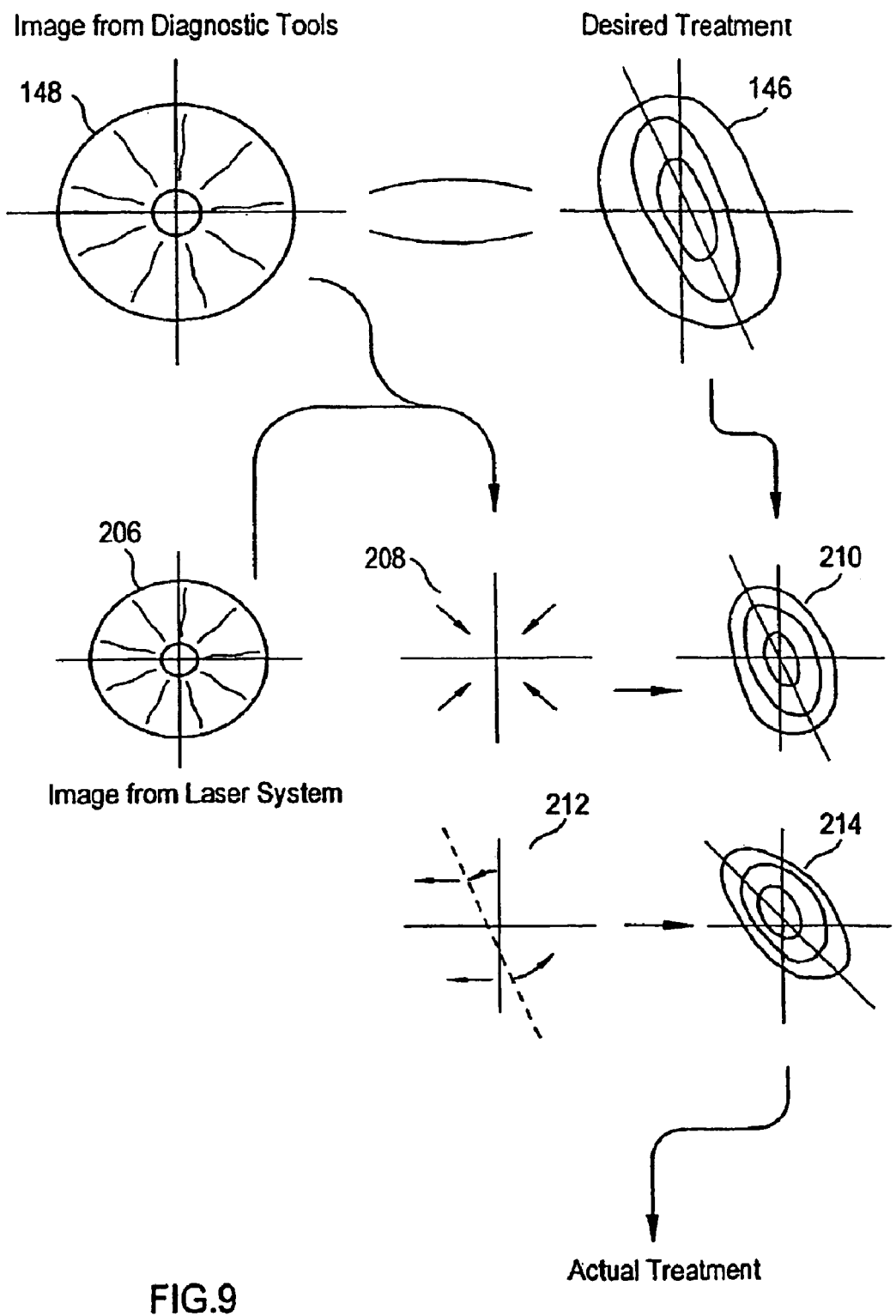
FIG. 9 is a flow diagram illustrating the use of stored iris data and imaged iris data to translate a desired treatment into an actual treatment.

Turning to FIG. 9, various adjustments that can be made to the desired treatment based upon the image of the actual iris I as received by the laser system 106 are illustrated. Referring again to FIG. 7C, the treatment generated 144 is provided as a desired treatment pattern 146 for controlling the laser system 106. The associated reference iris image data 148 from the diagnostic tools is used to align the treatment pattern 146 with the patient's eye E. The iris image 206 is provided by the pupil camera 154 of the laser system 106 and provided to the control system 156. The control system 156 compares the image 148, or the descriptors derived from that image, to the iris image 206. Based on the comparison, a variety of scaling functions is applied to the desired treatment 146. For example, it may be determined, based on the overall size of the actual iris image 206, that the treatment should be reduced in scale because of different focal distances of the diagnostic tools 100 or 102 and the laser system 106. So a scaling 208 is calculated and applied, yielding a scaled treatment 210. Then, it may be determined that the now scaled, desired treatment 210 must both be translated and rotated, as indicated by a translation and rotation function 212. This in turn is applied to the scaled desired treatment 210, yielding the actual treatment 214. These data are then used by the laser system 106 to perform an actual treatment.

Alternatively, if the control system 156 has great enough computational power, it is possible for each shot (i.e., laser pulse) to be appropriately rotated and translated. This may be desirable if the eye E displays a large degree of dynamic rotation and movement during the treatment, for example. Then, the iris image 206 can be tracked and the scaling functions 208 and 212 illustrated in FIG. 9 applied dynamically to each specific shot or sequence of shots in the desired treatment pattern 146. In this manner, the movement of the eye E can be accommodated shot-by-shot. This technique can be combined with the aiming laser technique of PCT/EP95/01287 such that the exact placement of each shot or series of shots relative to the iris image 206 is determined before the shot or shots are applied.

Therefore, in embodiments of the invention, any of a variety of diagnostic instruments can be fitted with a camera or other imager that acquires an image of the pupil, the iris, or other distinctive characteristics of the exterior of the eye and exports data corresponding to that image. Then, when a refractive treatment, such as an excimer laser treatment used in LASIK, is performed, the stored image (or its distinctive components) is compared to the actual image of the pupil, iris, or eye to align the laser such that the treatment will fall precisely as calculated.

Figure 10:
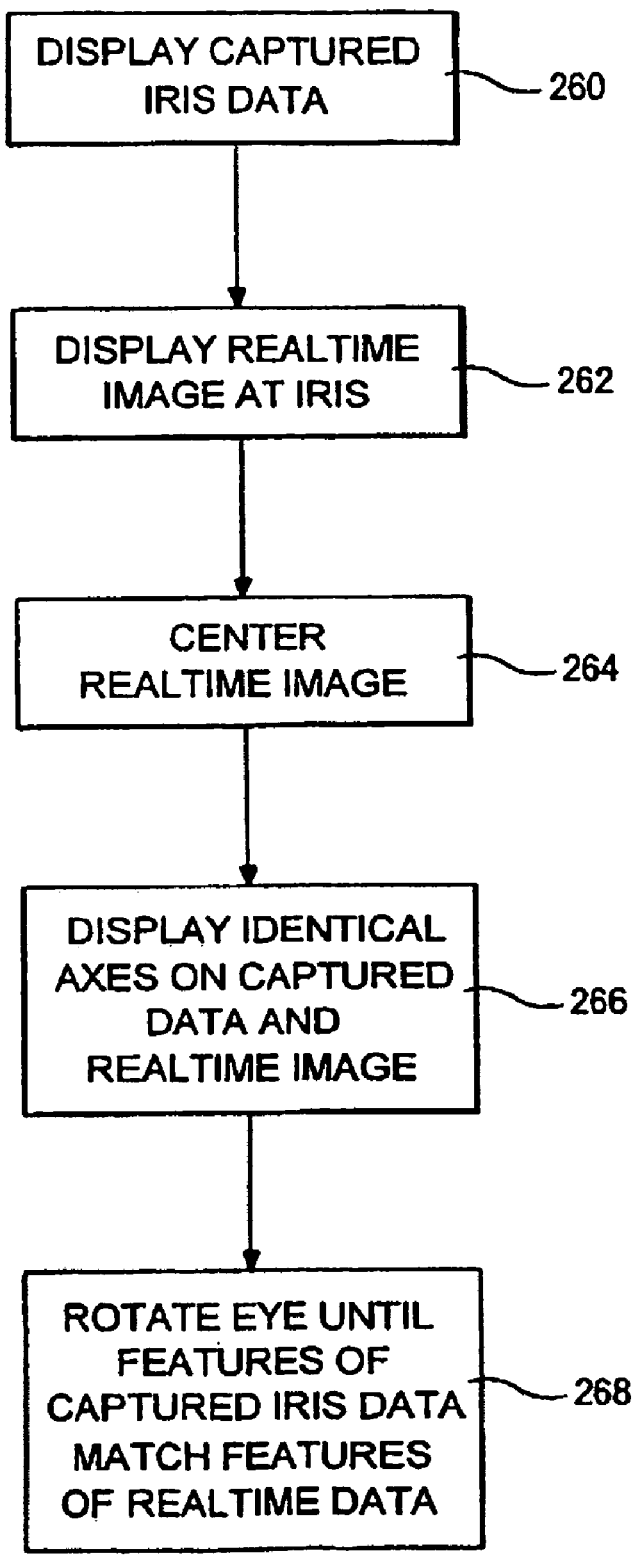
FIG. 10 is a flow diagram illustrating an alternative technique employing stored iris data to align a treatment.
Figure 11A:
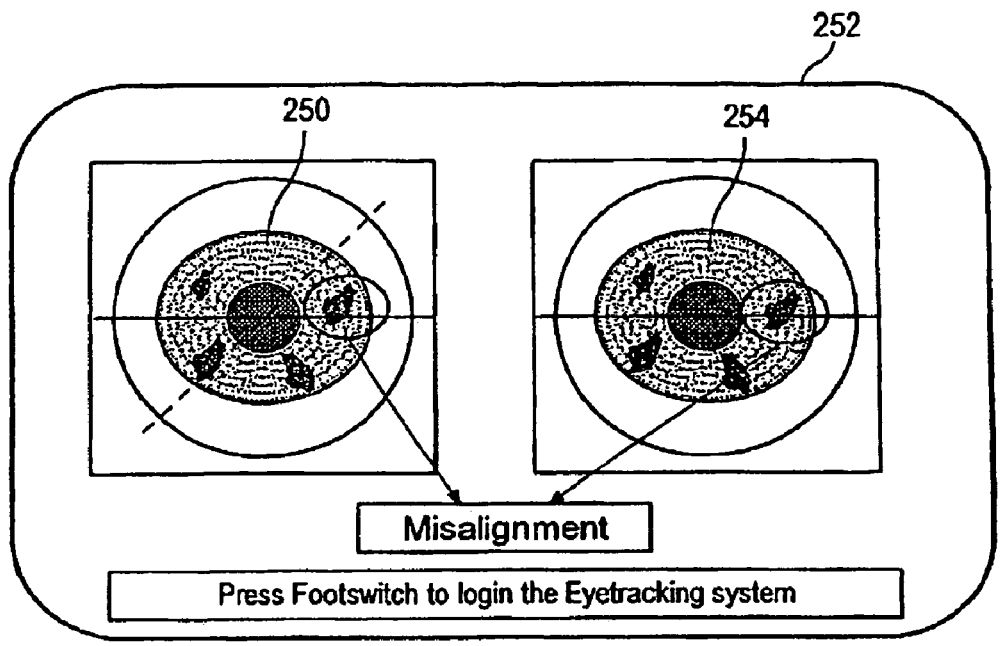
FIGS. 11A and 11B are display images illustrating the technique of FIG. 9.
Figure 11B:
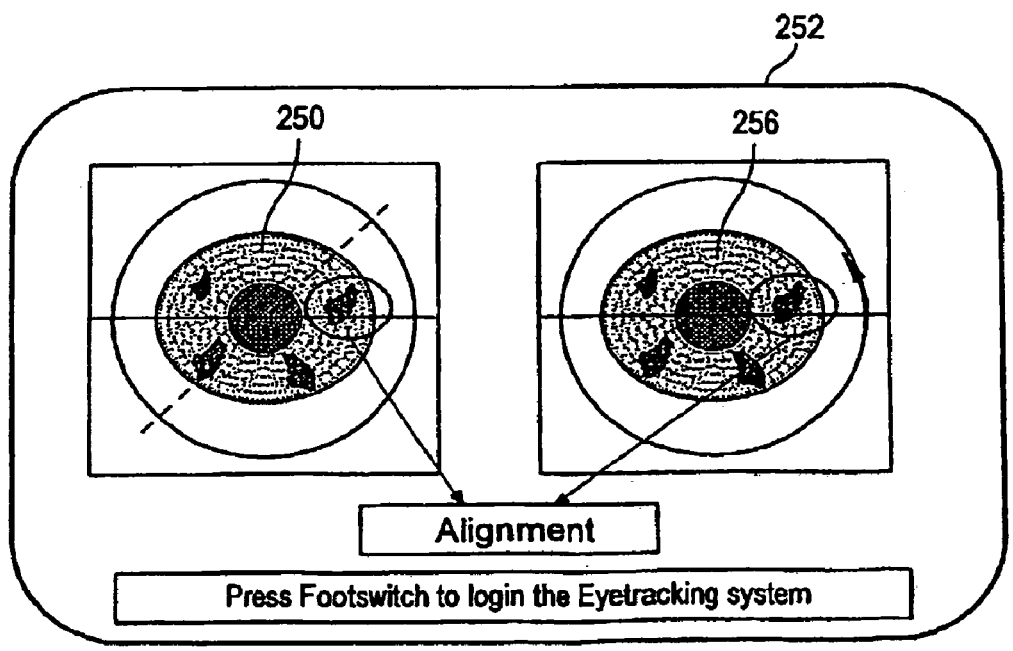

Turning to FIGS. 10 and 11A–11B, shown is an alternative technique to employ a previously captured image of an iris I to insure appropriate alignment of a laser treatment with the calculated treatment profile. Generally, FIG. 11A illustrates a display 252 provided by the camera 154 of the laser system 106 in FIG. 7C. On the left is captured iris I image data 250 captured when a refractive diagnostic tool was used to determine the refractive characteristics of the eye E. From this data, and coaligned with this iris I image data 250, a treatment profile had been developed. On the right side of the display 252 is real time iris I image 254, which is returned by the camera 154 of the laser system 106. As can be seen, the real time image 254 is slightly rotationally misaligned compared to the captured image data 250. This provides the physician with an opportunity to realign the patient's eye E, yielding in FIG. 11B a properly aligned real time iris I image 256. Preferably, the display includes reference axes that allow the physician to easily determine rotational misalignment. The system could also provide, for example, a cursor that the physician could place over identifying features to determine precisely the rotational location relative to the axis.

FIG. 10 illustrates the steps of using the system of FIGS. 11A and 11B in aligning the iris. First, the captured iris I image data 250 is displayed in a step 260. Simultaneously, the real time image 254 of the iris I is displayed at a step 262. When the excimer laser system 106 is a Keracor 217 employing an eye tracker, the physician then activates the eye tracker at a step 264, which centers the real time image 254. The eye tracking system on the Keracor 217 provides for centering the iris I, but does not provide for rotational alignment of the iris.

Proceeding to a step 266, an axis is displayed on both the captured data 250 and the real time image 254. The physician then compares the images on the screen, and determines an amount of rotation necessary to align the two images of the iris I. The physician then rotates the eye E so that the real time iris I image 256 rotationally corresponds to the captured iris image data 250. The physician can do this manually, such as using a suction ring or by repositioning the patient's head. Further, the system can provide for a "virtual" rotation of the patient's eye E by rotationally translating the treatment profile by an amount specified by the physician. In any case, the eye tracking system first provides for centering of the real time iris I image 254, and the physician then effects the rotational alignment of the iris I image 256 compared to the captured image data 250.

Other alternatives include a system in which the two images are superimposed. Also, if multiple diagnostic and refractive tools are used, different techniques can be used for alignment. For example, a wavefront tool could align its data based on the iris outline coupled with a rotational marker or an axis of astigmatism. A topography tool could use the same alignment bases, but also capture an iris image. A resultant, aligned treatment profile could then be aligned at the laser using the iris data alone. A variety of permutations could be used, and are described in assignee's concurrently filed application entitled "Iris Recognition and Tracking for Treatment of Optical Irregularities of the Eye". Further, a variety of user interface tools can assist the physician, including the aforementioned cursor positioning and the software rotation of the treatment profile.

The foregoing disclosure and description of the invention are illustrative and explanatory thereof, and various changes in the details of the illustrated apparatus and construction and method of operation may be made without departing from the spirit of the invention.

The invention claimed is:

1. A method of developing a refractive profile of an eye comprising the steps of:
   determining corneal topography data of the eye;
   determining wavefront aberration data of the eye;
   modifying one of the corneal topography data and the wavefront aberration data in view of the other of the corneal topography data and the wavefront aberration data combining data; and
   developing a refractive course of treatment of the eye from the modified one of the corneal topography data and the wavefront aberrations data.

2. The method of claim 1, wherein the step of determining corneal topography further comprises at least one of the following corneal topography techniques:
   employing a slit lamp, elevation based topography system to determine the topography of one or more refractive surfaces within the eye; and
   employing a corneal surface curvature based topography system to determine the topography of one or more refractive surface of the eye.

3. The method of claim 1, wherein developing comprises developing a photorefractive keratectomy course of treatment.

4. The method of claim 1, wherein developing comprises developing a laser in situ keratomileusis course of treatment.

5. The method of claim 1, wherein determining the corneal topography comprises employing an ultrasonic tool to determine the corneal topography.

6. The method of claim 1, wherein determining the corneal topography comprises determining a surface topography of a stronal surface of the cornea.

7. The method of claim 1, wherein determining the corneal topography comprises determining a surface topography of an epithelial surface of the cornea.

8. The method of claim 1, wherein determining the corneal topography and captured wavefront aberrations each comprise capturing an image of the iris of the eye, and wherein the step of combining comprises aligning determined wavefront aberration data and determined corneal topography data based on the iris image.

9. The method of claim 8, wherein capturing the iris image comprises capturing an iris image corresponding to the determined topography and wavefront aberrations.

10. The method of claim 1, wherein the step of developing a refractive course of treatment further comprises the steps of:
    evaluating the suitability of the eye for treatment based on the corneal topography, and
    developing the refractive course of treatment based on the captured wavefront aberration.

11. The method of claim 1, wherein the step of developing a refractive course of treatment further comprises:
    evaluating suitability of the eye for treatment based on the corneal topography; and
    employing only the corneal topography to develop a course of treatment for the eye if the eye is determined to be unsuitable for evaluating the wavefront aberrations.

12. The method of claim 1 further comprising the step of determining a calculated wavefront aberration of the eye based upon the determined corneal topography of the eye.

13. The method of claim 12, further comprising the step of adjusting the calculated wavefront aberration of the eye based upon the determined wavefront aberration of the eye.

14. The method of claim 12, further comprising comparing the calculated wavefront aberration of the eye with the determined wavefront aberration of the eye to validate suitability of proceeding with a course of treatment.

15. The method of claim 1, further comprising the step of displaying a simulation of the refractive course of treatment of the eye upon the determined corneal topography of the eye.

16. The method of claim 1, further comprising the steps of:
performing a course of refractive treatment on the eye;
evaluating the effectiveness of the course of refractive course of treatment of the eye; and
repeating the steps of determining corneal topography and determining wavefront aberration for providing a follow up course of treatment of the eye.

17. A system for determining refractive abnormalities of an eye, comprising:
a corneal topography tool adapted to provide corneal topography data of the eye;
a wavefront aberration tool adapted to provide a wavefront aberration data of the eye; and
a computational unit adapted to modify the wavefront aberration data in view of the corneal topography data to determine refractive abnormalities of the eye.

18. The system of claim 17, wherein the computational unit is adapted to receive the corneal topography data and the wavefront aberration data and combine the corneal topography data outside of a pupil area with the wavefront aberration data within the pupil area.

19. The system of claim 17, further comprising a camera adapted to capture an image of an iris of the eye that is used for alignment of the wavefront aberration data with the corneal topography data.

20. The system of claim 19, wherein the iris image corresponds to the wavefront aberration data and the corneal topography data.

21. The system of claim 17, further comprising:
a laser system adapted to provide a course of treatment for the eye based on the combined data.

22. The system of claim 21, wherein the laser system is coupled to the computational unit.

23. The system of claim 17, wherein the computational unit is adapted to calculate the wavefront aberration of the eye from the corneal topography data.

24. A system of claim 23, wherein the computational unit is adapted to compare the wavefront aberration data with the calculated wavefront aberration data to validate both.

25. The system of claim 23, wherein the computational unit is adapted to adjust the calculated wavefront aberration data based upon the wavefront aberration data provided by the wavefront aberration tool.

26. The system of claim 23, wherein the computational unit is adapted to calculate a course of refractive treatment.

27. The system of claim 26, wherein the computational unit is adapted to display a simulation of the course of refractive treatment as performed on the corneal topography data.

28. The system of claim 17, wherein the computational unit is distributed between the corneal topography tool and the wavefront aberration tool.

29. A method of developing a coarse of refractive treatment for an eye, the method comprising:
determining a corneal topography of the eye;
determining a wavefront aberration of the eye;
developing a course of refractive treatment based on determined wavefront aberration data; and
refining the course of refractive treatment based on the determined corneal topography data.

30. A system for determining refractive aberrations of an eye, comprising:
a corneal topography tool adapted to provide corneal topography data of the eye;
a topography system aberration tool adapted to calculate corneal wavefront aberration data of the eye from the corneal topography data; and
a computational unit adapted to receive the corneal wavefront aberration data and to develop a course of refractive treatment based on the corneal wavefront aberration data.

31. The system of claim 30, further comprising;
a laser system coupled to the computational unit, the laser system adapted to receive the modified course of treatment for laser surgery of the eye.

32. The system of claim 31, wherein the laser system is located physically remote from the computational unit.

33. The system of claim 32, wherein the laser system comprises the computational unit.

34. A system for developing a course of refractive treatment for an eye, comprising:
a corneal topography tool adapted to provide corneal topography data of the eye;
a wavefront aberration tool adapted to provide a wavefront aberration data of the eye; and
a computational unit adapted to evaluate one of the data sets for patient suitability for refractive treatment and to employ the other data set to develop a treatment profile, if the eye is determined to be suitable for refractive treatment.

35. The system of claim 34, wherein the computational unit evaluates the patient suitability based on the topography data and prepares the treatment profile based on the wavefront data.

* * * * *